United States Patent [19]

Gray et al.

[11] Patent Number: 5,055,468
[45] Date of Patent: Oct. 8, 1991

[54] USE OF BRIDGED TRICYCLIC AMINE DERIVATIVES AS ANTI-ISCHEMIC AGENTS

[75] Inventors: Nancy M. Gray, Buffalo Grove; Patricia C. Contreras, Evanston, both of Ill.

[73] Assignee: G. D. Searle & Co., Chicago, Ill.

[21] Appl. No.: 428,531

[22] Filed: Oct. 30, 1989

[51] Int. Cl.$^5$ .................. A61K 31/495; A61K 31/50; A61K 31/135

[52] U.S. Cl. .................................. 514/249; 514/252; 514/255; 514/656

[58] Field of Search ............... 514/650, 255, 249, 252, 514/656

[56] References Cited

U.S. PATENT DOCUMENTS 3,422,104 1/1969 Schröter et al. .................... 544/154

FOREIGN PATENT DOCUMENTS 482642 1/1970 Switzerland.

OTHER PUBLICATIONS

S. M. Rothman and J. W. Olney, "Glutamate and the Pathophysiology of Hypoxia—Ischemic Brain Damage", *Anals of Neurology*, vol. 19, No. 2 (1986).
P. L. Wood et al, *Neuropharm.*, 21, 1235–1238 (1982).
C. Carter et al, *J. Pharm. Exp. Ther.*, 247 (3), 1222–1232 (1988).
K. Rehse et al, *Arch. Pharm.* (*Neinheim*), 320, 839–836 (1987).
S. Lecolir, *Chim. Ther.*, 3, 34–38 (1968).
J. R. Boissier et al, *J. Med. Chem.*, 10, 86–91 (1967).

*Primary Examiner*—Frederick E. Waddell
*Assistant Examiner*—Terry L. Wilson
*Attorney, Agent, or Firm*—J. Timothy Keane; Paul D. Matukaitis

[57] ABSTRACT

Certain bridged tricyclic amine compounds are described as being therapeutically effective in treatments of CNS disorders resulting from neurotoxic damage or neurodegenerative diseases, particularly those CNS disorders resulting from ischemic events. Compounds of particular interest for use as neuroprotective agents are those of the formula

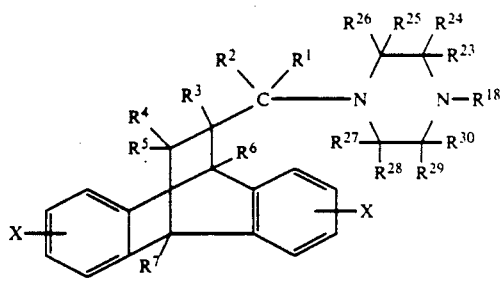

wherein each of $R^1$ and $R^2$ is independently selected from hydrido, loweralkyl, benzyl and phenyl; wherein each of $R^1$ through $R^7$ is independently selected from hydrido, loweralkyl, hydroxy, benzyl, phenyl, loweralkoxy, phenoxy, benzyloxy, halo and haloloweralkyl; wherein $R^{18}$ may be selected from hydrido, loweralkyl, cycloalkyl of five or six carbon atoms, cycloalkylalkyl of six or seven carbon atoms, phenyl, hydroxyloweralkyl, and heteroaryl selected from saturated or fully unsaturated heterocyclic rings containing five to seven ring members of which one or two ring members are nitrogen atom; wherein each X is independently one or more groups selected from hydrido, hydroxy, loweralkyl, benzyl, phenyl, loweralkoxy, phenoxy, halolower-alkyl, halo, and lower-alkanoyl; and wherein each of $R^{23}$ through $R^{30}$ is independently selected from hydrido, lower alkyl, benzyl, phenyl and halo; wherein $R^{18}$ together with one of $R^{23}$, $R^{24}$, $R^{29}$ or $R^{30}$ may form a fused heterocyclic ring containing five or six ring members; or a pharmaceutically-acceptable salt thereof.

15 Claims, No Drawings

USE OF BRIDGED TRICYCLIC AMINE DERIVATIVES AS ANTI-ISCHEMIC AGENTS

FIELD OF THE INVENTION

This invention is in the field of clinical neurology and relates specifically to a class of therapeutically useful compounds, compositions and methods for management of neurotoxic damage or neurodegenerative diseases. For example, these compounds are particularly useful for treating neurotoxic injury which follows periods of hypoxia, anoxia or ischemia associated with stroke, cardiac arrest or perinatal asphyxia.

BACKGROUND OF THE INVENTION

Unlike other tissues which can survive extended periods of hypoxia, brain tissue is particularly sensitive to deprivation of oxygen or energy. Permanent damage to neurons can occur during brief periods of hypoxia, anoxia or ischemia. Neurotoxic injury is known to be caused or accelerated by certain excitatory amino acids (EAA) found naturally in the central nervous system (CNS). Glutamate (Glu) is an endogenous amino acid which has been characterized as a fast excitatory transmitter in the mammalian brain. Glutamate is also known as a powerful neurotoxin capable of killing CNS neurons under certain pathological conditions which accompany stroke and cardiac arrest. Normal glutamate concentrations are maintained within brain tissue by energy-consuming transport systems. Under low energy conditions which occur during conditions of hypoglycemia, hypoxia or ischemia, cells can release glutamate. Under such low energy conditions the cell is not able to take glutamate back into the cell. Initial glutamate release stimulates further release of glutamate which results in an extracellular glutamate accumulation and a cascade of neurotoxic injury.

It has been shown that the sensitivity of central neurons to hypoxia and ischemia carn be reduced by either blockage of synaptic transmission or by the specific antagonism of postsynaptic glutamate receptors [see S. M. Rothman and J. W. Olney, "Glutamate and the Pathophysiology of Hypoxia - Ischemic Brain. Damage," *Annals of Neurology*, Vol. 19, No. 2 (1986)]. Glutamate is characterized as a broad spectrum agonist having activity at three neuronal excitatory amino acid receptor sites. These receptor sites are named after the amino acids which selectively excite them, namely: Kainate (KA), N-methyl-D-aspartate (NMDA or NMA) and quisqualate (QUIS).

Neurons which have EAA receptors on their dendritic or somal surfaces undergo acute excitotoxic degeneration when these receptors are excessively activated by glutamate. Thus, agents which selectively block or antagonize the action of glutamate at the EAA synaptic receptors of central neurons can prevent neurotoxic injury associated with hypoxia, anoxia, or ischemia caused by stroke, cardiac arrest or perinatal asphyxia.

It is known that compounds of various structures, such aminophosphonovalerate derivatives and piperidine dicarboxylate derivatives, may act as competitive antagonists at the NMDA receptor and also block the increase in cyclic GMP levels due to the presence of excitatory amino acids [P. L. Wood et al, *Neuropharm.*, 21, 1235-1238 (1982)].

Certain piperidineethanol derivatives, such as ifenprodil and (±)-α-(4-chlorophenyl)-4-[(4-fluorophenyl)methyl]-1-piperidineethanol, which are known anti-ischemic agents, have been found to be non-competitive NMDA receptor antagonists which also block the increase of cyclic GMP levels due to the presence of excitatory amino acids [C. Carter et al, *J. Pharm Exp. Ther.*, 247 (3), 1222-1232 (1988)].

Ethanoanthracene-type compounds have been identified for other pharmaceutical uses. For example tricyclic oligoamine compounds, such as N,N'-bis-(4-phenylbutyl)-9,10-dihydro-9,10-ethanoanthracene-11,12bis-methylamine, has been mentioned for use as inhibitors of platelet aggregation (K. Rehse et al, *Arch. Pharm. (Neinheim)*, 320, 829-836 (1987)]. A class of dihydro-9,10-ethano-9,10-anthracene compounds, including 9,10-dihydro-1,2-(1-pyrrolidinylmethyl)-9,10-ethanoanthracen-11-one, have been evaluated for analgesic activity [S. Lecolier, *Chim. Ther.*, 3, 34–38 (1968)]. Certain 9,10-dihydro-9,10-ethanoanthracene derivatives, including N-[(9,10-dihydro-9,10-ethanoanthracenyl)methyl]-N,N',N'-trimethylethylenediamine, 4-[(9,10-dihydro-9,10-ethanoanthracenyl)methyl]-1-methylpiperizine and 1-[(9,10-dihydro-9,10-ethanoanthracenyl)methyl]piperidine have been described as having anticholinergic, antihistaminic, local anesthetic or hypotensive properties [J. R. Boissier et al, *J. Med. Chem.*, 10, 86–91 (1967)]. U.S. Pat. No. 3,422,104 describes 9,10-dihydro-9,10-ethanoanthracene compounds, including N-[(9,10-dihydro-9,10-ethanoanthracenyl)methyl]dimethylamine, 4-[(9,10-dihydro-9,10-ethanoanthracenyl)methyl]-1(2-hydroxyethyl)piperizine and 1-[(9,10-dihydro-9,10-ethanoanthracenyl)-ethyl]piperidine for use as a spasmolytic or in treatment of depression. Swiss Pat. No. 482,642 describes certain 11-aminoalkyl-9,10-dihydro-9,10-ethanoanthracenes, including N-[(9,10-dihydro-9,10-ethanoanthracenyl)methyl]methylamine, 4-methylpiperazide of 9,10-dihydro-9,10-ethanoanthracene-11-carboxylic acid and 1-[(9,10-dihydro-9,10-ethanoanthracenyl)ethyl]piperidine as anesthetics.

DESCRIPTION OF THE INVENTION

Treatment of a mammal afflicted by or susceptible to a neurodegenerative disease or neurotoxic injury is provided by administering to the mammal a therapeutically-effective amount of one or more compounds selected from a class of bridged tricyclic amine derivatives defined by Formula I:

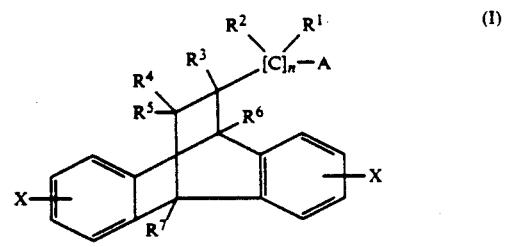

wherein A is a group selected from

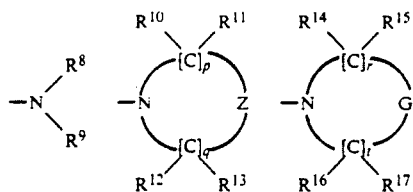

wherein each of $R^1$ and $R^2$ is independently selected from hydrido, alkyl, cycloalkyl, cycloalkylalkyl, aralkyl, aryl, hydroxyalkyl, alkoxyalkyl and halo; wherein $R^1$ and $R^2$ may be taken together to form oxo; wherein each of $R^3$ through $R^7$ is independently selected from hydrido, alkyl, hydroxy, cycloalkyl, cycloalkylalkyl, aralkyl, aryl, alkoxy, alkoxyalkyl, aryloxy, aralkoxy, hydroxyalkyl, halo and haloalkyl; wherein $R^4$ and $R^5$ may be taken together to form oxo; wherein n is a number selected from zero to five, inclusive; wherein each X is independently one or more groups selected from hydrido, hydroxy, alkyl, cycloalkyl, cycloalkylalkyl, aralkyl, aryl, alkoxy, aralkoxy, aryloxy, alkoxyalkyl, haloalkyl, hydroxyalkyl, halo, cyano, amino, monoalkylamino, dialkylamino, nitro, carboxy, carboxyalkyl and alkanoyl; wherein each of $R^8$ and $R^9$ is independently selected from hydrido, alkyl, cycloalkyl, cycloalkylalkyl, monoalkylaminoalkyl, dialkylaminoalkyl, aralkyl, aryl, alkoxyalkyl and hydroxyalkyl; wherein each of $R^{10}$ through $R^{13}$ is independently selected from hydrido, alkyl, cycloalkyl, cycloalkylalkyl, aralkyl, aryl, alkoxyalkyl, hydroxyalkyl and halo; wherein $R^{10}$ and $R^{11}$ may be taken together to form oxo; wherein $R^{12}$ and $R^{13}$ may be taken together to form oxo; wherein each of p and q is a number selected from one to four, inclusive; wherein Z is selected from O, S, $>N-R^{18}$, $>SO$ and $>SO_2$; wherein $R^{18}$ may be selected from hydrido, alkyl, cycloalkyl, cycloalkylalkyl, aryl, aralkyl, heteroaryl, alkoxyalkyl, hydroxyalkyl, alkanoyl, aralkanoyl, aroyl, aminoalkyl, monoalkylaminoalkyl and dialkylaminoalkyl; wherein $R^{18}$ together with one of $R^{10}$ through $R^{13}$ may form a fused heterocyclic ring containing five to about eight ring members; wherein each of $R^{14}$ through $R^{17}$ is independently selected from hydrido, alkyl, cycloalkyl, cycloalkylalkyl, aralkyl, aryl, alkoxyalkyl, hydroxyalkyl and halo; wherein $R^{14}$ and $R^{15}$ may be taken together to form oxo; wherein $R^{16}$ and $R^{17}$ may be taken together to form oxo; wherein each of r and t is a number independently selected from one to four, inclusive; wherein G is selected to form a heterocyclic ring containing one or more groups independently selected from

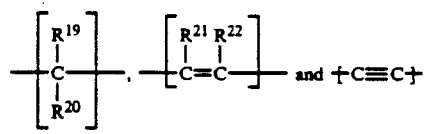

wherein each of $R^{19}$ through $R^{22}$ is independently selected from hydrido, hydroxy, alkyl, cycloalkyl, cycloalkylalkyl, aralkyl, aryl, alkoxy, aralkoxy, aryloxy, alkoxyalkyl, haloalkyl, hydroxyalkyl, halo, cyano, amino, monoalkylamino, dialkylamino, carboxy, carboxyalkyl and alkanoyl; or a pharmaceutically-acceptable salt thereof.

A first family of preferred compounds within Formula I consists of compounds of Formula II

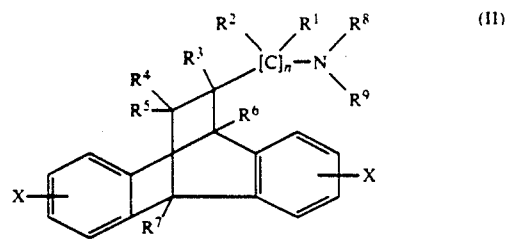

wherein each of $R^1$ and $R^2$ is independently selected from hydrido, alkyl, cycloalkyl, cycloalkylalkyl, aralkyl, aryl, hydroxyalkyl, alkoxyalkyl and halo; wherein $R^1$ and $R^2$ may be taken together to form oxo; wherein each of $R^3$ through $R^7$ is independently selected from hydrido, alkyl, hydroxy, cycloalkyl, cycloalkylalkyl, aralkyl, aryl, alkoxy, alkoxyalkyl, aryloxy, aralkoxy, hydroxyalkyl, halo and haloalkyl; wherein $R^4$ and $R^5$ may be taken together to form oxo; wherein n is a number selected from zero to five, inclusive; wherein each X is independently one or more groups selected from hydrido, hydroxy, alkyl, cycloalkyl, cycloalkylalkyl, aralkyl, aryl, alkoxy, aralkoxy, aryloxy, alkoxyalkyl, haloalkyl, hydroxyalkyl, halo, cyano, amino, monoalkylamino, dialkylamino, nitro, carboxy, carboxyalkyl and alkanoyl; wherein each of $R^8$ and $R^9$ is independently selected from hydrido, alkyl, cycloalkyl, cycloalkylalkyl, monoalkylaminoalkyl, dialkylaminoalkyl, aralkyl, aryl, alkoxyalkyl, and hydroxyalkyl; or a pharmaceutically-acceptable salt thereof.

A preferred family of compounds within Formula II consists of compounds wherein each of $R^1$ and $R^2$ is independently selected from hydrido, alkyl, cycloalkyl, cycloalkylalkyl, aralkyl, aryl, hydroxyalkyl, alkoxyalkyl and halo; wherein $R^1$ and $R^2$ may be taken together to form oxo; wherein each of $R^3$ through $R^7$ is independently selected from hydrido, alkyl, hydroxy, cycloalkyl, cycloalkylalkyl, phenalkyl, phenyl, alkoxy, alkoxyalkyl, phenoxy, phenalkoxy, hydroxyalkyl, halo and haloalkyl; wherein $R^4$ and $R^5$ may be taken together to form oxo; wherein n is a number from zero to five, inclusive; wherein each X is independently one or more groups selected from hydrido, hydroxy, alkyl, cycloalkyl, cycloalkylalkyl, phenalkyl, phenyl, alkoxy, phenalkoxy, phenoxy, alkoxyalkyl, haloalkyl, hydroxyalkyl, halo, cyano, amino, monoalkylamino, dialkylamino, carboxy, carboxyalkyl and alkanoyl; wherein each of $R^8$ and $R^9$ is independently selected from hydrido, alkyl, cycloalkyl, cycloalkylalkyl, monoalkylaminoalkyl, dialkylaminoalkyl, phenalkyl, phenyl, alkoxyalkyl and hydroxyalkyl; or a pharmaceutically-acceptable salt thereof.

A more preferred family of compounds within Formula II consists of compounds wherein each of $R^1$ and $R^2$ is independently selected from hydrido, loweralkyl, phenylloweralkyl, phenyl and loweralkoxyloweralkyl; wherein $R^1$ and $R^2$ may be taken together to form oxo; wherein each of $R^3$ through $R^7$ is independently selected from hydrido, loweralkyl, hydroxy, cycloalkyl of three to eight carbon atoms, cycloalkylalkyl of four to eight carbon atoms, phenylloweralkyl, phenyl, loweralkoxy, loweralkoxyloweralkyl, phenoxy, phenalkoxy, hydroxyloweralkyl, halo and haloloweralkyl; wherein $R^4$ and $R^5$ may be taken together to form oxo; wherein n is a number selected from zero to five, inclusive; wherein each X is independently one or more groups selected from hydrido, hydroxy, loweralkyl, cycloalkyl of three to about eight carbon atoms, cycloalkylalkyl of four to about eight carbon atoms, phenylloweralkyl, phenyl, loweralkoxy, phenoxy, loweralkoxyloweralkyl, haloloweralkyl, hydroxyloweralkyl, halo, carboxy, carboxyloweralkyl and loweralkanoyl; wherein each of $R^8$ and $R^9$ is independently selected from hydrido, loweralkyl, cycloalkyl of three to about eight carbon atoms, cycloalkylalkyl of four to about eight carbon atoms, phenylloweralkyl, phenyl, monoalkylaminoalkyl, dialkylaminoalkyl, loweralkoxyloweralkyl and hydroxyloweralkyl; or a pharmaceutically-acceptable salt thereof.

A highly preferred family of compounds within Formula II consists of compounds wherein each of $R^1$ and $R^2$ is independently selected from hydrido, loweralkyl, benzyl and phenyl; wherein $R^1$ and $R^2$ may be taken together to form oxo; wherein n is selected from zero to two, inclusive; wherein each of $R^3$ through $R^7$ is independently selected from hydrido, loweralkyl, hydroxy, benzyl, phenyl, loweralkoxy, phenoxy, benzyloxy, halo and haloloweralkyl; wherein each X is independently one or more groups selected from hydrido, hydroxy, loweralkyl, benzyl, phenyl, loweralkoxy, phenoxy, haloloweralkyl, halo and loweralkanoyl; wherein each of $R^8$ and $R^9$ is independently selected from hydrido, loweralkyl, benzyl, phenyl, monoloweralkylaminoloweralkyl, diloweralkylaminoloweralkyl, loweralkoxyloweralkyl and hydroxyloweralkyl; or a pharmaceutically-acceptable salt thereof.

A more highly preferred family of compounds within Formula II consists of compounds wherein each of $R^1$ and $R^2$ is independently hydrido or methyl; wherein $R^1$ and $R^2$ may be taken together to form oxo; wherein each of $R^3$ through $R^7$ is independently selected from hydrido, methyl, ethyl, hydroxy, methoxy, halo and trihalomethyl; wherein each of $R^8$ and $R^9$ may be independently selected from hydrido, methyl, ethyl, hydroxymethyl, hydroxyethyl, dimethylaminoethyl and diethylaminoethyl; wherein n is one or two; and wherein each X is independently one or more groups selected from hydrido, methyl, ethyl, hydroxy, methoxy, trihalomethyl and halo; or a pharmaceutically-acceptable salt thereof.

Specific compounds of most interest within Formula II are N-diethylaminoethyl-9,10-dihydro-9,10-ethanoanthracene-11-carboxamide; N-diethylaminoethyl-9,10-dibromo-9,10-dihydro-9,10-ethanoanthracene-11-methyl-11-carboxamide; and N-(2-hydroxyethyl)-N-methyl-9,10-dihydro-9,10-ethanoanthracenylmethylamine, of which the last compound is of highest interest.

A second family of preferred compounds within Formula I consists of compounds of Formula III:

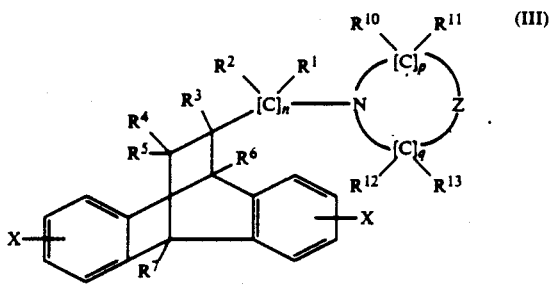

(III)

wherein each of $R^1$, $R^2$ and $R^{10}$ through $R^{13}$ is independently selected from hydrido, alkyl, cycloalkyl, cycloalkylalkyl, aralkyl, aryl, alkoxyalkyl, hydroxyalkyl and halo; wherein $R^{10}$ and $R^{11}$ may be taken together to form oxo; wherein $R^{12}$ and $R^{13}$ may be taken together to form oxo; wherein $R^1$ and $R^2$ may be taken together to form oxo; wherein each of $R^3$ through $R^7$ is independently selected from hydrido, alkyl, hydroxy, cycloalkyl, cycloalkylalkyl, aralkyl, aryl, alkoxy, alkoxyalkyl, aryloxy, aralkoxy, hydroxyalkyl, halo and haloalkyl; wherein $R^4$ and $R^5$ may be taken together to form oxo; wherein n is a number selected from zero to five, inclusive; wherein each of p and q is a number selected from one to four, inclusive; wherein Z is selected from O, S, >N—$R^{18}$, >SO and >SO$_2$; wherein $R^{18}$ may be selected from hydrido, alkyl, cycloalkyl, cycloalkylalkyl, aryl, aralkyl, heteroaryl, alkoxyalkyl, hydroxyalkyl, alkanoyl, aralkanoyl, aroyl, aminoalkyl, monoalkylaminoalkyl and dialkylaminoalkyl; wherein $R^{18}$ together with one of $R^{10}$ through $R^{13}$ may form a fused heterocyclic ring containing five to about eight ring members; wherein each X is independently one or more groups selected from hydrido, hydroxy, alkyl, cycloalkyl, cycloalkylalkyl, aralkyl, aryl, alkoxy, aralkoxy, aryloxy, alkoxyalkyl, haloalkyl, hydroxyalkyl, halo, cyano, amino, monoalkylamino, dialkylamino, nitro, carboxy, carboxyalkyl and alkanoyl; or a pharmaceutically-acceptable salt thereof.

A preferred family of compounds within Formula III consists of compounds wherein each of $R^1$, $R^2$ and $R^{10}$ through $R^{13}$ is independently selected from hydrido, alkyl, cycloalkyl, cycloalkylalkyl, phenalkyl, phenyl, alkoxyalkyl, hydroxyalkyl and halo; wherein $R^1$ and $R^2$ may be taken together to form oxo; wherein each of $R^3$ through $R^7$ is independently selected from hydrido, alkyl, hydroxy, cycloalkyl, cycloalkylalkyl, phenalkyl, phenyl, alkoxy, alkoxyalkyl, phenoxy, phenalkoxy, hydroxyalkyl, halo and haloalkyl; wherein $R^4$ and $R^5$ may be taken together to form oxo; wherein n is a number from zero to five, inclusive; wherein each of p and q is a number selected from one to four, inclusive; wherein Z is selected from O, S and N—$R^{18}$; wherein $R^{18}$ may be selected from hydrido, alkyl, cycloalkyl, cycloalkylalkyl, phenyl, phenalkyl, heteroaryl, alkoxyalkyl, hydroxyalkyl, alkanoyl, phenalkanoyl, aroyl, aminoalkyl, monoalkylaminoalkyl and dialkylaminoalkyl; wherein $R^{18}$ together with one of $R^{10}$ through $R^{13}$ form a fused heterocyclic ring containing five to about eight ring members; wherein each X is independently one or more groups selected from hydrido, hydroxy, alkyl, cycloalkyl, cycloalkylalkyl, phenalkyl, phenyl, alkoxy, phenalkoxy, phenoxy, alkoxyalkyl, haloalkyl, hydroxyalkyl, halo, cyano, amino, monoalkylamino, dialkylamino, carboxy, carboxyalkyl and alkanoyl; or a pharmaceutically-acceptable salt thereof.

A more preferred family of compounds within Formula III consists of compounds wherein each of $R^{10}$ through $R^{13}$ is independently selected from hydrido, loweralkyl, cycloalkyl of three to about eight carbon atoms, cycloalkylalkyl of four to about eight carbon atoms, phenylloweralkyl, phenyl, loweralkoxyloweralkyl, hydroxyloweralkyl and halo; wherein each of $R^1$ and $R^2$ is independently selected from hydrido, loweralkyl, phenylloweralkyl, phenyl and loweralkoxyloweralkyl; wherein $R^1$ and $R^2$ may be taken together to form oxo; wherein each of $R^3$ through $R^7$ is independently selected from hydrido, loweralkyl, hydroxy, cycloalkyl of three to eight carbon atoms, cycloalkylalkyl of four to eight carbon atoms, phenylloweralkyl, phenyl, loweralkoxy, loweralkoxyloweralkyl, phenoxy, phenalkoxy, hydroxyloweralkyl, halo and haloloweralkyl;

wherein R⁴ and R⁵ may be taken together to form oxo; wherein n is a number selected from zero to five, inclusive; wherein each of p and q is two or three; wherein Z is selected from O, S, >N—R¹⁸; wherein R¹⁸ may be selected from hydrido, loweralkyl, cycloalkyl of three to about eight carbon atoms, cycloalkylalkyl of four to about eight carbon atoms, phenyl, phenylloweralkyl, loweralkoxyloweralkyl, hydroxyloweralkyl, loweralkanoyl and heteroaryl selected from saturated, partially unsaturated and fully unsaturated heterocyclic rings containing five to seven ring members of which one or two ring members are selected from oxygen atom and nitrogen atom; wherein R¹⁸ together with one of R¹⁰ through R¹³ may form a fused heterocyclic ring containing five or six ring members; wherein each X is independently one or more groups selected from hydrido, hydroxy, loweralkyl, cycloalkyl of three to about eight carbon atoms, cycloalkylalkyl of four to about eight carbon atoms, phenylloweralkyl, phenyl, loweralkoxy, phenoxy, loweralkoxyloweralkyl, haloloweralkyl, hydroxyloweralkyl, halo, carboxy, carboxyloweralkyl and loweralkanoyl; or a pharmaceutically-acceptable salt thereof.

A highly preferred family of compounds within Formula III consists of compounds of Formula IV:

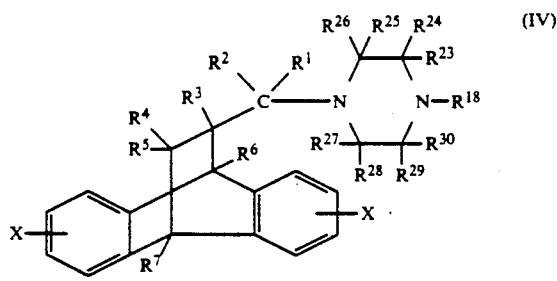

wherein each of R¹ and R² is independently selected from hydrido, loweralkyl, benzyl and phenyl; wherein R¹ and R² may be taken together to form oxo; wherein each of R³ through R⁷ is independently selected from hydrido, loweralkyl, hydroxy, benzyl, phenyl, benzyl, loweralkoxy, phenoxy, benzyloxy, halo and haloloweralkyl; wherein R¹⁸ may be selected from hydrido, loweralkyl, cycloalkyl of five or six carbon atoms, cycloalkylalkyl of six or seven carbon atoms, phenyl, hydroxyloweralkyl, and heteroaryl selected from saturated or fully unsaturated heterocyclic rings containing five to seven ring members of which one or two ring members are nitrogen atom; wherein each X is independently one Or more groups selected from hydrido, hydroxy, loweralkyl, benzyl, phenyl, loweralkoxy, phenoxy, haloloweralkyl, halo, and loweralkanoyl; and wherein each of R²³ through R³⁰ is independently selected from hydrido, loweralkyl, benzyl, phenyl and halo; wherein R¹⁸ together with one of R²³, R²⁴, R²⁹ or R³⁰ may form a fused heterocyclic ring containing five or six ring members; or a pharmaceutically-acceptable salt thereof.

A more highly preferred family of compounds consists of compounds within Formula IV wherein each of R¹ and R² is independently hydrido or methyl; wherein R¹ and R² may be taken together to form oxo; wherein each of R³ through R⁷ is independently selected from hydrido, methyl, ethyl, hydroxy, methoxy, halo and trihalomethyl; wherein R¹⁸ is selected from hydrido, methyl, ethyl, hydroxyethyl, benzyl, pyridyl and pyrimidyl; wherein each of R²³ through R³⁰ is independently selected from hydrido, methyl, ethyl and trihalomethyl; wherein R¹⁸ together with one of R²³, R²⁴, R²⁹ or R³⁰ may form a fused heterocyclic ring containing five or six ring members; and wherein each X is independently one or more groups selected from hydrido, methyl, ethyl, hydroxy, methoxy, trihalomethyl and halo; or a pharmaceutically-acceptable salt thereof.

Specific compounds of most interest within Formula IV are 4-[(9,10-dihydro-9,10-ethanoanthracenyl)methyl]-1-methylpiperazine; 4-[(9,10-dihydro-9,10-ethanoanthracenyl)methyl]-1-(2-hydroxyethyl)-piperazine; 4-[(9,10-dihydro-9,10-ethanoanthracenyl)methyl]-1-(2-pyrimidyl)piperazine; 4-[(9,10-dihydro-9,10-ethanoanthracenyl)methyl-1,4-diazabicyclo[4.3.0]-nonane; 4-[(9,10-dihydro-9,10-ethanoanthracenyl)carbonyl-]1-methylpiperazine; and 4-[(9,10-dihydro-9,10-ethanoanthracenyl)methyl]-1-benzylpiperazine.

Of highest interest are the compounds 4-[(9,10-dihydro-9,10-ethanoanthracenyl)methyl]-1-(2-pyrimidyl)-piperazine; 4-[(9,10-dihydro-9,10-ethanoanthracenyl)-methyl]-1,4-diazabicyclo[4.3.0]nonane; and 4-[(9,10-dihydro-9,10-ethanoanthracenyl)methyl]-1-benzylpiperazine.

A third family of preferred compounds within Formula I consists of compounds of Formula V:

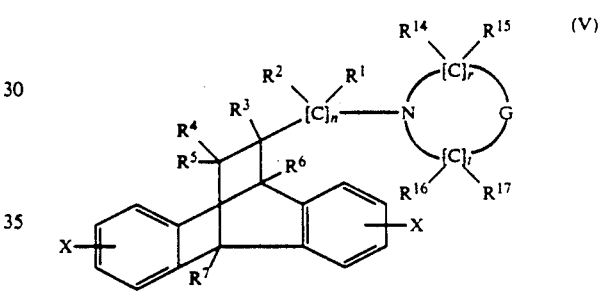

wherein each of R¹, R² and R¹⁴ through R¹⁷ is independently selected from hydrido, alkyl, cycloalkyl, cycloalkylalkyl, aralkyl, aryl, alkoxyalkyl, hydroxyalkyl and halo; wherein R¹ and R² may be taken together to form oxo wherein R¹⁴ and R¹⁵ may be taken together to form oxo; wherein R¹⁶ and R¹⁷ may be taken together to form oxo; wherein each of R³ through R⁷ is independently selected from hydrido, alkyl, hydroxy, cycloalkyl, cycloalkylalkyl, aralkyl, aryl, alkoxy, alkoxyalkyl, aryloxy, aralkoxy, hydroxyalkyl, halo and haloalkyl; herein R⁴ and R⁵ may be taken together to form oxo; wherein n is a number selected from zero to five, inclusive; wherein each of r and t is a number independently selected from one to four; wherein each X is independently one or more groups selected from hydrido, hydroxy, alkyl, cycloalkyl, cycloalkylalkyl, aralkyl, aryl, alkoxy, aralkoxy, aryloxy, alkoxyalkyl, haloalkyl, hydroxyalkyl, halo, cyano, amino, monoalkylamino, dialkylamino, nitro, carboxy, carboxyalkyl and alkanoyl; wherein G is selected to form a heterocyclic ring containing one or more groups independently selected from

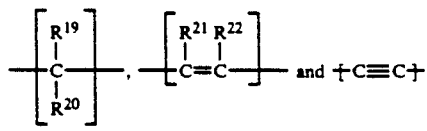

wherein each of $R^{19}$ through $R^{22}$ is independently selected from hydrido, hydroxy, alkyl, cycloalkyl, cycloalkylalkyl, aralkyl, aryl, alkoxy, aralkoxy, aryloxy, alkoxyalkyl, haloalkyl, hydroxyalkyl, halo, cyano, amino, monoalkylamino, dialkylamino, carboxy, carboxyalkyl and alkanoyl; or a pharmaceuticallyacceptable salt thereof.

A preferred family of compounds within Formula V consists of compounds wherein each of $R^1$, $R^2$ and $R^{14}$ through $R^{17}$ is independently selected from hydrido, alkyl, cycloalkyl, cycloalkylalkyl, phenalkyl, phenyl, alkoxyalkyl, hydroxyalkyl and halo; wherein $R^1$ and $R^2$ may be taken together to form oxo; wherein each of $R^3$ through $R^7$ is independently selected from hydrido, alkyl, hydroxy, cycloalkyl, cycloalkylalkyl, phenalkyl, phenyl, alkoxy, alkoxyalkyl, phenoxy, phenalkoxy hydroxyalkyl, halo and haloalkyl; wherein $R^4$ and $R^5$ may be taken together to form oxo; wherein n is a number from zero to five, inclusive; wherein each of r and t is a number independently selected from one to four, inclusive; wherein each X is independently one or more groups selected from hydrido, hydroxy, alkyl, cycloalkyl, cycloalkylalkyl, phenalkyl, phenyl, alkoxy, phenalkoxy, phenoxy, alkoxyalkyl, haloalkyl, hydroxyalkyl, halo, cyano, amino, monoalkylamino, dialkylamino, carboxy, carboxyalkyl and alkanoyl; wherein G is selected to form a heterocyclic ring containing one or more groups independently selected from

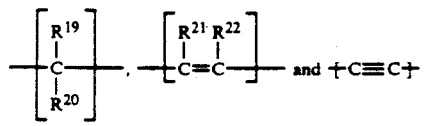

wherein each of $R^{19}$ through $R^{22}$ is independently selected from hydrido, hydroxy, alkyl, cycloalkyl, cycloalkylalkyl, phenalkyl, phenyl, alkoxy, phenoxy, phenalkoxy, alkoxyalkyl, haloalkyl, hydroxyalkyl, halo, amino, monoalkylamino, dialkylamino, and alkanoyl; or a pharmaceutically-acceptable salt thereof.

A more preferred family of compounds within Formula V consists of compounds wherein each of $R^{14}$ through $R^{17}$ is independently selected from hydrido, loweralkyl, cycloalkyl of three to about eight carbon atoms, cycloalkylalkyl of four to about eight carbon atoms, phenylloweralkyl, phenyl, loweralkoxyloweralkyl, hydroxyloweralkyl and halo; wherein each of $R^1$ and $R^2$ is independently selected from hydrido, loweralkyl, phenylloweralkyl, phenyl and loweralkoxyloweralkyl; wherein $R^1$ and $R^2$ may be taken together to form oxo; wherein each of $R^3$ through $R^7$ is independently selected from hydrido, loweralkyl, hydroxy, cycloalkyl of three to eight carbon atoms, cycloalkylalkyl of four to eight carbon atoms, phenylloweralkyl, phenyl, loweralkoxy, loweralkoxyloweralkyl, phenoxy, phenalkoxy, hydroxyloweralkyl, halo and haloloweralkyl; wherein $R^4$ and $R^5$ may be taken together to form oxo; wherein n is a number selected from zero to five, inclusive; wherein each of r and t is independently two or three; wherein each X is independently one or more groups selected from hydrido, hydroxy, loweralkyl, cycloalkyl of three to about eight carbon atoms, cycloalkylalkyl of four to about eight carbon atoms, phenylloweralkyl, phenyl, loweralkoxy, phenoxy, loweralkoxyloweralkyl, haloloweralkyl, hydroxyloweralkyl, halo, carboxy, carboxyloweralkyl and loweralkanoyl; wherein G is selected to form a heterocyclic ring containing one or more groups independently selected from

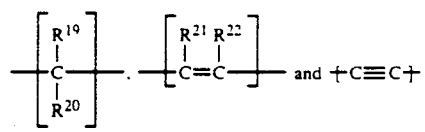

wherein each of $R^{19}$ through $R^{22}$ is independently selected from hydrido, hydroxy, loweralkyl, cycloalkyl of three to eight carbon atoms, cycloalkylalkyl of four to eight carbon atoms, phenyl, phenylloweralkyl, alkoxy, phenoxy, phenylloweralkoxy, alkoxyalkyl, haloalkyl, hydroxyalkyl, halo, amino, monoalkylamino, dialkylamino and alkanoyl; or a pharmaceutically-acceptable salt thereof.

A highly preferred family of compounds within Formula V consists of compounds of Formula VI:

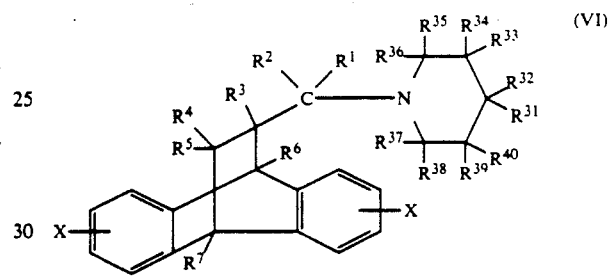

wherein each of $R^1$ and $R^2$ is independently selected from hydrido, loweralkyl, benzyl and phenyl; wherein each of $R^3$ through $R^7$ is independently selected from hydrido, loweralkyl, hydroxy, benzyl, phenyl, benzyl, loweralkoxy, phenoxy, benzyloxy, halo and haloloweralkyl; wherein each X is independently one or more groups selected from hydrido, hydroxy, loweralkyl, benzyl, phenyl, loweralkoxy, phenoxy, haloloweralkyl, halo, and loweralkanoyl; and wherein each of $R^{31}$ through $R^{40}$ is independently selected from hydrido, loweralkyl, benzyl, phenyl and halo; or a pharmaceutically-acceptable salt thereof.

A more highly preferred family of compounds consists of compounds within Formula VI wherein each of $R^1$ and $R^2$ is independently hydrido or methyl; wherein each of $R^3$ through $R^7$ is independently selected from hydrido, methyl, ethyl, hydroxy, methoxy, halo and trihalomethyl; wherein each of $R^{31}$ through $R^{40}$ is independently selected from hydrido, methyl, ethyl, benzyl and phenyl; and wherein each X is independently one or more groups selected from hydrido, methyl, ethyl, hydroxy, methoxy, trihalomethyl and halo.

Specific compounds of most interest within Formula VI are compound is selected from 4-benzyl-1-[(9,10-dihydro-9,10-ethanoanthracenyl)methyl]piperidine; 1-[(9,10-dihydro-9,10-ethanoanthracenyl)methyl]-4-phenylpiperidine; and 1-[(9,10-dihydro-9,10-ethanoanthracenyl)methyl]piperidine. Of highest interest are the compounds 4-benzyl-1-[(9,10-dihydro-9,10-ethanoanthracenyl)methyl]piperidine; and 1-[(9,10-dihydro-9,10-ethanoanthracenyl)methyl-4-phenylpiperidine.

The compounds of Formula I through Formula III would be particularly useful to treat patients having neurodegenerative disorders for treating neurotoxic injury.

The phrase "therapeutically-effective amount" means that amount of one or more compounds of Formula I which provides a therapeutic benefit in treatment or management of neurotoxic injury resulting from a CNS disorder or traumatic event or in treatment or management of a neurodegenerative disease. Examples of traumatic events which may result in neurotoxic injury are hypoxia, anoxia and ischemia associated with perinatal asphyxia, cardiac arrest or stroke. In treatment of such traumatic-event-related cases, a "therapeutically-effective amount" of a compound of Formula I would be an antineurotoxic or an antiexcitotoxic amount of the compound which is effective to reduce or prevent such neurotoxic injury by inhibiting, for example, excessive amounts of excitotoxin from being generated near or attaching to excitatory amino acid receptors. In cases of treatment of a neurodegenerative disease, the amount of a "therapeutically-effective amount" of a compound of Formula I would be that amount effective to reduce or prevent neurodegeneration arising from or causing CNS disorders such as convulsions and epilepsy.

The term "hydrido" denotes a single hydrogen atom (H) which may be attached, for example, to an oxygen atom to form an hydroxyl group. Where the term "alkyl" is used, either alone or within other terms such as "haloalkyl", "aralkyl" and "hydroxyalkyl", the term "alkyl" embraces linear or branched radicals having one to about ten carbon atoms unless otherwise specifically described. Preferred alkyl radicals are "lower alkyl" radicals having one to about five carbon atoms. The term "cycloalkyl" embraces radicals having three to ten carbon atoms, such as cyclopropyl, cyclobutyl, cyclohexyl and cycloheptyl. An example of "cycloalkylalkyl" is cyclohexylmethyl. The term "haloalkyl" embraces radicals wherein any one or more of the carbon atoms is substituted with one or more halo groups, preferably selected from bromo, chloro and fluoro. Specifically embraced by the term "haloalkyl" are monohaloalkyl, dihaloalkyl and polyhaloalkyl groups. A monohaloalkyl group, for example, may have either a bromo, a chloro, or a fluoro atom within the group. Dihaloalkyl and polyhaloalkyl groups may be substituted with two or more of the same halo groups, or may have a combination of different halo groups. Examples of a dihaloalkyl group are dibromomethyl, dichloromethyl and bromochloromethyl. Examples of a polyhaloalkyl are trifluoromethyl, 2,2,2-trifluoroethyl, perfluoroethyl and 2,2,3,3-tetrafluoropropyl groups. The term "alkoxy" embraces linear or branched oxy-containing radicals having an alkyl portion of one to about ten carbon atoms, such as methoxy, ethoxy, isopropoxy and butoxy. An example of "cycloalkyloxy" is cyclohexyloxy. An example of "alkoxyalkyl" is methoxymethyl. An example of "aralkyloxy" is benzyloxy. The term "alkylthio" embraces radicals containing a linear or branched alkyl group, of one to about ten carbon atoms attached to a divalent sulfur atom, such as a methylthio group. The term "aryl" embraces aromatic radicals such as phenyl, naphthyl and biphenyl. The term "aralkyl" embraces aryl-substituted alkyl radicals such as benzyl, diphenylmethyl, triphenylmethyl, phenylethyl, phenylbutyl and diphenylethyl. The terms "benzyl" and "phenylmethyl" are interchangeable. The terms "aryloxy" and "arylthio" denote radical respectively, aryl groups having an oxygen or sulfur atom through which the radical is attached to a nucleus, examples of which are phenoxy and phenylthio. The terms "sulfinyl" and "sulfonyl", whether used alone or linked to other terms, denotes respectively divalent radicals $>SO$ and $>SO_2$. The terms "monoalkylamino" and "dialkylamino" denote amino groups which have been substituted, respectively, with one alkyl radical and with two alkyl radicals. The term "acyl" whether used alone, or within a term such as acyloxy, denotes a radical provided by the residue after removal of hydroxyl from an organic acid, examples of such radical being acetyl and benzoyl. The term "heteroaryl" embraces aromatic ring systems containing one or two hetero atoms selected from oxygen, nitrogen and sulfur in a ring system having five or six ring members, examples of which are thienyl, furanyl, pyridinyl, thiazolyl, pyrimidyl and isoxazolyl. The phrase, as used above, "$R^{18}$ together with one of $R^{23}$, $R^{24}$, $R^{29}$ and $R^{30}$ may form a fused heterocyclic ring containing five or six members", is intended to embrace a bicyclic fused heterocyclic ring system which includes both hetero atoms contained in Formula III and Formula IV, which ring system may be further substituted as described herein. An example of such bicyclic fused ring system is shown as Compound No. 4, herein.

Within this class of compounds of the invention are the pharmaceutically acceptable salts of the compounds of Formula I, including acid addition salts and base addition salts. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, p-hydroxybenzoic, salicyclic, phenylacetic, mandelic, embonic (pamoic), methansulfonic, ethanesulfonic, 2-hydroxyethanesulfonic, pantothenic, benzenesulfonic, toluenesulfonic, sulfanilic, mesylic, cyclohexylaminosulfonic, stearic, algenic, β-hydroxybutyric, malonic, galactaric and galacturonic acid. Suitable pharmaceutically-acceptable base addition salts of compounds of Formula I include metallic salts made from aluminium, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of Formula I by reacting, for example, the appropriate acid or base with the compound of Formula I.

Compounds of general Formula I can possess one or more asymmetric carbon atoms and are thus capable of existing in the form of optical isomers as well as in the form of racemic or non-racemic mixtures thereof. The optical isomers can be obtained by resolution of the racemic mixtures according to conventional processes, for example by formation of diastereoisomeric salts by treatment with an optically active acid or base. Examples of appropriate acids are tartaric, diacetyltartaric, dibenzoyltartaric, ditoluoyltartaric and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of Formula I with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of Formula I can likewise be obtained by utilizing optically active starting materials. These isomers may be in the form of a free acid, a free base, an ester or a salt.

General Synthetic Procedures

Compounds of Formula I may be prepared in accordance with the following generic procedures, which show preparation of three different families of compounds containing three different amino terminal groups.

Generic Procedure I

This general procedure of Step 1 applies to preparation of all three families.

Step 1(a):

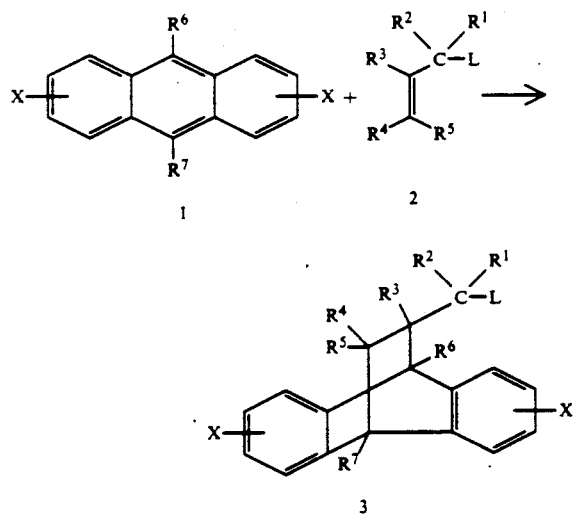

wherein X and $R^1$ through $R^7$ are as previously described; and wherein L is halogen, tosylate, mesylate, brosylate or OH.

A process for preparing the compounds of the invention starts with anthracenes of general structure 1 where X, $R^6$ and $R^7$ have the value assigned previously. The anthracene is combined with alkenes of general structure 2 where $R^1$ through $R^5$ have the value assigned previously and L is a good leaving group such as chloro, bromo, mesylate, tosylate or OH. The reaction is best achieved by mixing the reagents neat or in a solvent like benzene, toluene, or xylenes. The reaction temperature can vary from about 150° C. to about 250° C.

Step 1(b):

Alternately, compounds of general structure 3 can be prepared according to the following generic procedure:

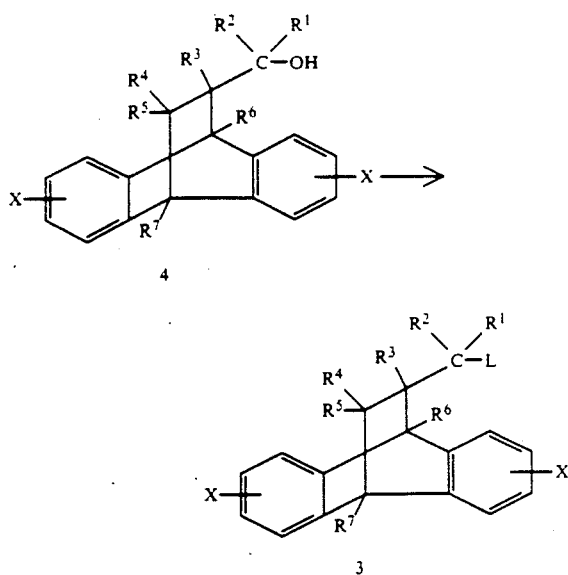

wherein X and $R^1$ through $R^7$ are as previously described; and wherein L is halogen, tosylate, mesylate, or brosylate. The compounds of general structure 3 thus can be prepared by mixing the alcohol 4 with a reagent such as thionyl chloride, phosphorous oxychloride, triphenylphosphine dibromide, methanesulfonyl chloride and p-toluenesulfonyl chloride. The reagents can be combined neat or in a variety of aprotic solvents such as carbon tetrachloride, toluene, tetrahydrofuran, or ether. The temperature of the reaction may vary from room temperature to reflux of the reaction mixture.

The following Steps 2(a)(i), 2(a)(ii), 2(a)(iii), 2(b)(i), 2(b)(ii) and 2(b)(iii) describes displacement reactions to make each of the three families of compounds.

Step 2(a)(i):

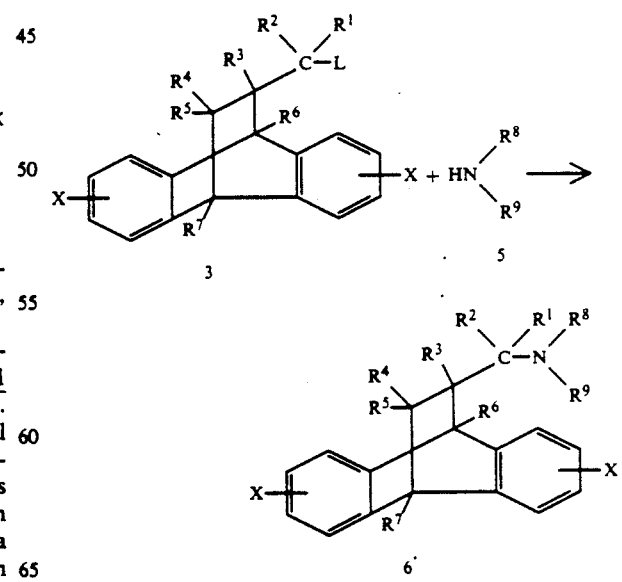

wherein X, L and $R^1$ through $R^9$ are as previously described.

In the second step of the process, amines of general structure 6 are prepared by combining compounds of general structure 3 with amines of general structure 5, wherein $R^8$ and $R^9$ are as defined before. The compounds can be combined in a variety of solvents such as toluene, xylenes, dimethylformamide, hexamethylphosphoramide or ethanol. The temperature of the reaction can vary from room temperature to reflux of the reaction mixture.

Step 2(b)(i):

Alternately, amines of general structure 6 can be prepared according to the following generic procedure:

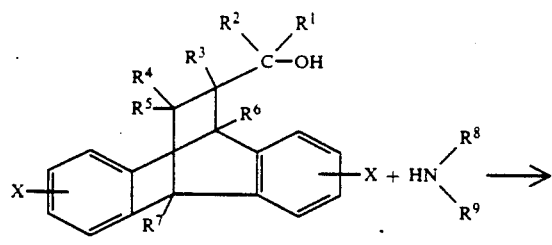

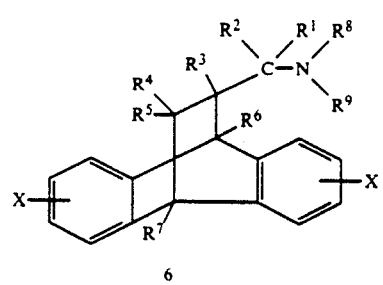

wherein X and $R^1$ through $R^9$ are as previously described.

In Step 2(b) of the process, amines of general structure 6 are prepared by combining an alcohol of general structure 4 with amines of general structure 5, where $R^8$ and $R^9$ are as previously defined. The compounds can be combined in a variety of aprotic solvents such as toluene, xylenes, dimethylformamide, or hexamethylphosphoramide. The conversion requires combining the two reagents in the solvent in the presence of a strong base such as sodium hydride and in the presence of an activating agent such as triphenylphosphine, N-methyl-N-phenylaminotriphenylphosphonium iodide or similar reagents. The temperature of the reaction can vary from room temperature to about 100° C.

Step 2(a)(ii):

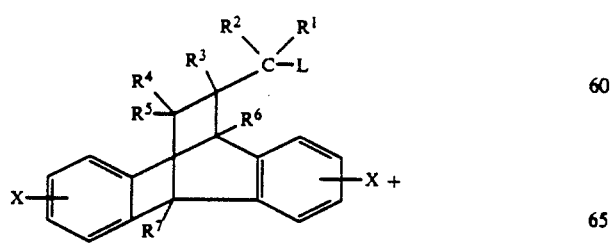

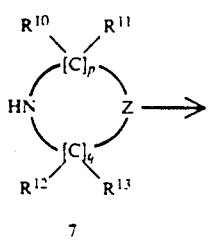

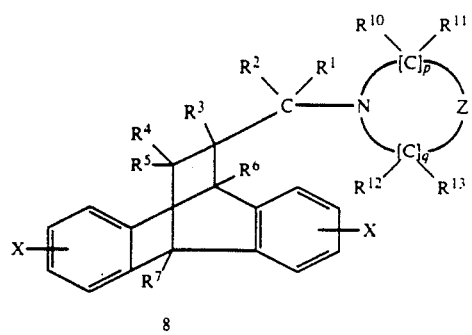

wherein p, q, X, L and $R^1$ through $R^7$ and $R^{10}$ through $R^{13}$ are as previously described.

In the second step of the process, amines of general structure 8 are prepared by combining compounds of general structure 3 with amines of general structure 7, where p, q, Z, and $R^{10}$ through $R^{13}$ are as previously defined. The compounds can be combined in a variety of solvents such as toluene, xylenes, dimetlylformamide, hexamethylphosphoramide or ethanol. The temperature of the reaction can vary from room temperature to reflux of the reaction mixture.

Step 2(b)(ii):

Alternately, amines of general structure 6 can be prepared according to the following generic procedure:

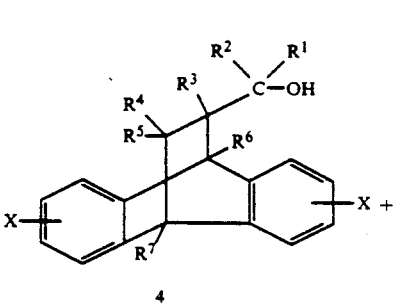

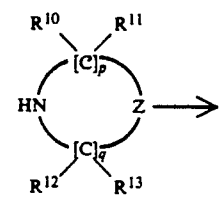

-continued

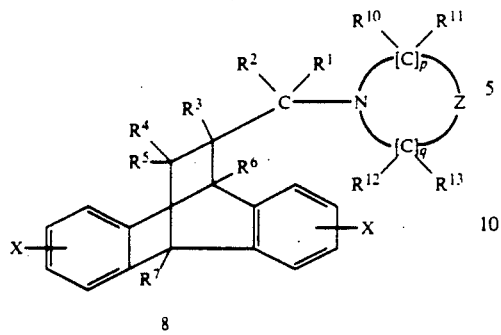
8 wherein p, q, X, Z and $R^1$ through $R^7$ and $R^{10}$ through $R^{13}$ are as previously described.

In Step 2(b) of the process, amines of general structure 8 are prepared by combining an alcohol of general structure 4 with amines of general structure 7, where p, q, E and $R^{10}$ through $R^{13}$ are as previously defined. The compounds can be combined in a variety of aprotic solvents such as toluene, xylenes, dimethylformamide, or hexamethylphosphoramide. The conversion requires combining the two reagents in the solvent in the presence of a strong base such as sodium hydride and in the presence of an activating agent such as triphenylphosphine, N-methyl-N-phenylaminotriphenylphosphonium iodide or similar reagents. The temperature of the reaction can vary from room temperature to about 100° C.

A preferred method for preparing compounds by Generic Procedure I involves the displacement reaction of Step 2 wherein compound of Formula IV:

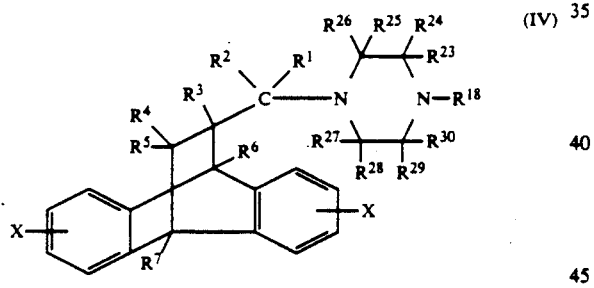
(IV)

wherein each of $R^1$ and $R^2$ is independently selected from hydrido, loweralkyl, benzyl and phenyl; wherein each of $R^3$ through $R^7$ is independently selected from hydrido, loweralkyl, hydroxy, benzyl, phenyl, loweralkoxy, phenoxy, benzyloxy, halo and haloloweralkyl; wherein $R^{18}$ may be selected from hydrido, loweralkyl, cycloalkyl of five or six carbon atoms, cycloalkylalkyl of six or seven carbon atoms, phenyl, benzyl, hydroxyloweralkyl, and heteroaryl selected from saturated or fully unsaturated heterocyclic rings containing five to seven ring members of which one or two ring members are nitrogen atom; wherein each X is independently one or more groups selected from hydrido, hydroxy, loweralkyl, benzyl, phenyl, loweralkoxy, phenoxy, haloloweralkyl halo, and loweralkanoyl; and wherein each of $R^{23}$ through $R^{30}$ is independently selected from hydrido, loweralkyl, benzyl, phenyl and halo; wherein $R^{18}$ together with one of $R^{23}$, $R^{24}$, $R^{29}$ or $R^{30}$ may form a fused heterocyclic ring containing five or six ring members; or a pharmaceutically-acceptable salt thereof; said method comprising reacting a compound of the formula

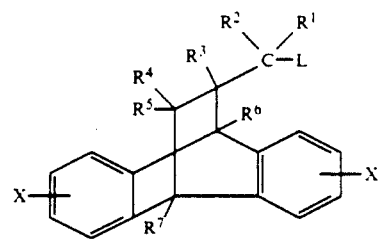

wherein each of $R^1$ through $R^7$ and X is defined above; and wherein L is selected from halo, hydroxy, paratoluenesulfonyloxy, methylsulfonyloxy and parabromotoluenesulfonyloxy; with an amine of the formula

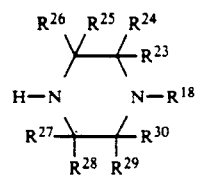

wherein each of $R^{18}$ and $R^{23}$ through $R^{30}$ is as defined above.

Step 2(a)(iii):

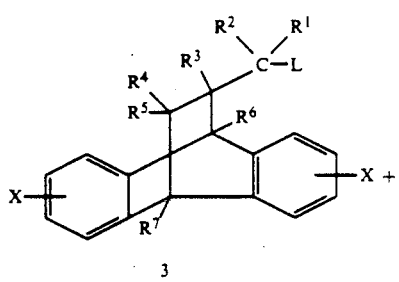
3

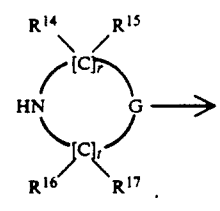
9

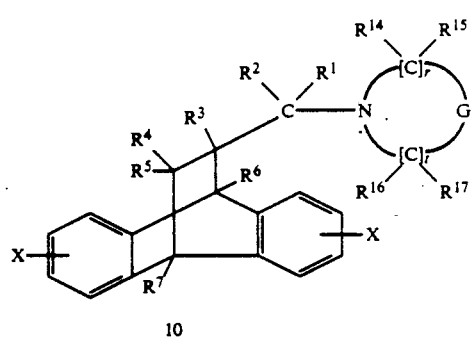
10 wherein p, q, G, X, L and $R^1$ through $R^{17}$ are as previously described.

In the second step of the process, amines of general structure 10 are prepared by combining compounds of general structure 3 with amines of general structure 9, where r, t, G, and $R^{14}$ through $R^{17}$ are as previously defined. The compounds can be combined in a variety of solvents such as toluene, xylenes, dimethylformamide, hexamethylphosphoramide or ethanol. The temperature of the reaction can vary from room temperature to reflux of the reaction mixture.

Step 2(b)(iii):

Alternately, amines of general structure 6 can be prepared according to the following generic procedure:

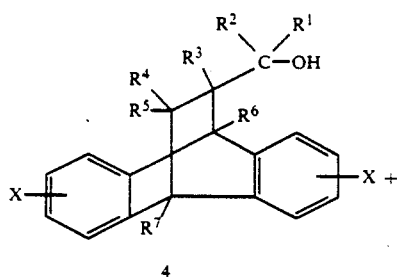

4

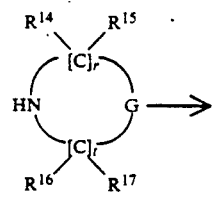

9

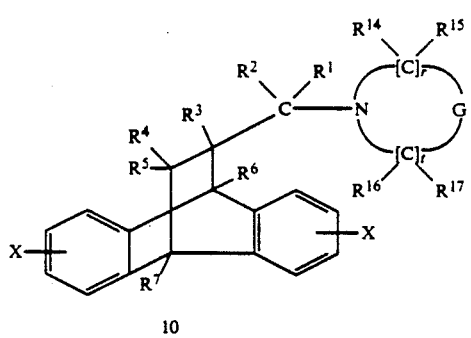

10 wherein r, t, G, X and $R^1$ through $R^{17}$ are as previously described.

In Step 2(b) of the process, amines of general structure 10 are prepared by combining an alcohol of general structure 4 with amines of general structure 9, where r, t, G and $R^{14}$ through $R^{17}$ are as previously defined. The compounds can be combined in a variety of aprotic solvents such as toluene, xylenes, dimethylformamide, or hexamethylphosphoramide. The conversion requires combining the two reagents in the solvent in the presence of a strong base such as sodium hydride and in the presence of an activating agent such as triphenylphosphine, N-methyl-N-phenylaminotriphenylphosphonium iodide or similar reagents. The temperature of the reaction can vary from room temperature to about 100° C.

A preferred method for preparing compounds by Generic Procedure I involves the displacement reaction of Step 2 wherein compound of Formula VI:

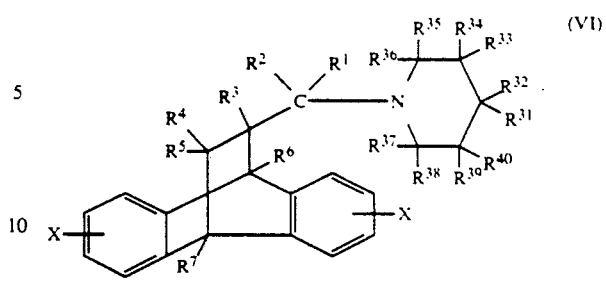

wherein each of $R^1$ and $R^2$ is independently selected from hydrido, loweralkyl, benzyl and phenyl; wherein each of $R^3$ through $R^7$ is independently selected from hydrido, loweralkyl, hydroxy, benzyl, phenyl, loweralkoxy, phenoxy, benzyloxy, halo and haloloweralkyl; wherein each X is independently one or more groups selected from hydrido, hydroxy, loweralkyl, benzyl, phenyl, loweralkoxy, phenoxy, haloloweralkyl, halo, and loweralkanoyl; and wherein each of $R^{31}$ through $R^{40}$ is independently selected from hydrido, loweralkyl, benzyl, phenyl and halo; or a pharmaceutically-acceptable salt thereof; said method comprising reacting a compound of the formula

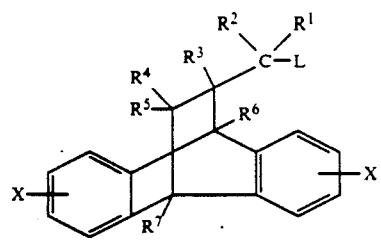

wherein each of $R^1$ through $R^7$ and X is defined above; and wherein L is selected from halo, hydroxy, paratoluenesulfonyloxy, methylsulfonyloxy and parabromotoluenesulfonyloxy; with an amine of the formula

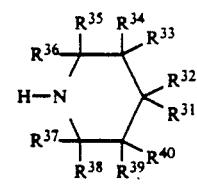

wherein each of $R^{31}$ through $R^{40}$ is as defined above.

Generic Procedure II

In this general description, preparation of all three families of compounds are identical for Steps 1-3, shown below:

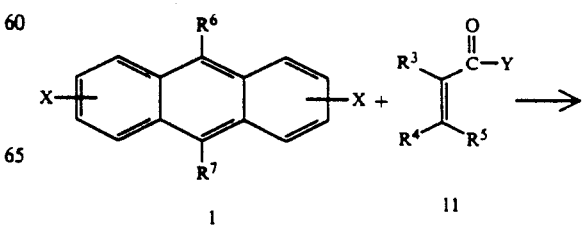

1            11

-continued

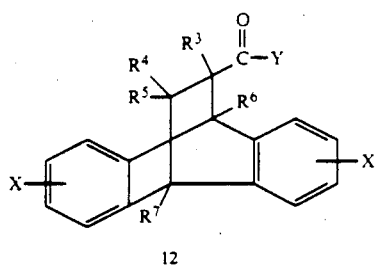
12

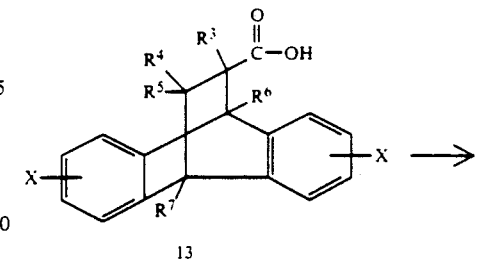
13 wherein X and R³ through R⁷ are as defined before; and wherein Z is selected from lower alkoxy or benzyloxy.

An alternate process that can be used to synthesize the products of the invention starts with anthracenes of general structure 1 where X, R⁶ and R⁷ have the values assigned previously. The anthracene 1 is combined with acrylates of general structure 11 where Z and R³ through R⁵ have the value assigned previously. The reaction is best achieved by mixing the reagents neat or in a solvent like benzene, toluene, or xylenes. The reaction temperatures can vary from about 150° C. to about 250° C.

Step 2:

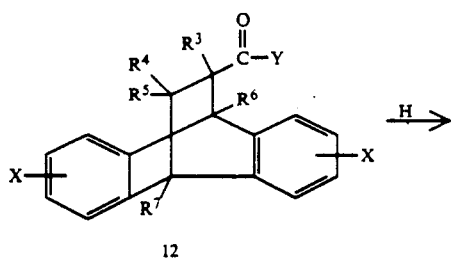
12

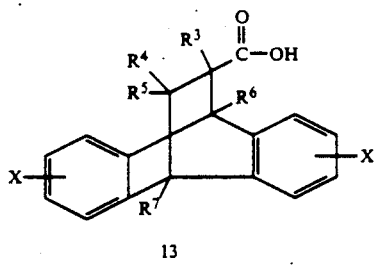
13 wherein X and R³ through R⁷ are as defined before; wherein Z is selected from lower alkoxy or benzyloxy; wherein A is selected from a variety of bases such as sodium hydroxide, lithium hydroxide or potassium hydroxide.

In the second step of the process, the ester 12 is hydrolyzed to the acid 13 by mixing the ester with water in the presence of a base such as sodium hydroxide, lithium hydroxide or potassium hydroxide. The reaction is best achieved by mixing the reagents neat or in a solvent such as ethanol or methanol. The reaction temperature can vary from about room temperature to reflux of the reaction mixture.

Step 3

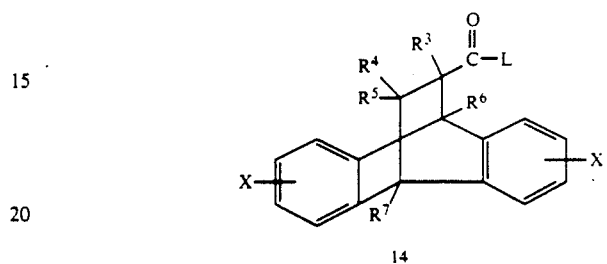
14 wherein X and R³ through R⁷ are as defined before; and wherein L represents a good leaving group such as chloro, bromo, or acyl.

In the third step of the process, the acid 13 is converted to a compound of the general structure 14, where L is a good leaving group such as chloro, bromo or acyl. The conversion can be best achieved by mixing the acid 13 with reagents such as thionyl chloride, phosphorous oxychloride, phosphorous tribromide, or other reagents. This conversion is best achieved by mixing the reagents neat or in an aprotic solvent such as tetrahydrofuran, methylene chloride, or ether. The temperature of the reaction can vary from room temperature to reflux of the reaction mixture.

The following steps 4(i), 4(ii), 4(iii), 5(i), 5(ii) and 5(iii) describe displacement steps for making each of the three families of compounds: Step 4(i):

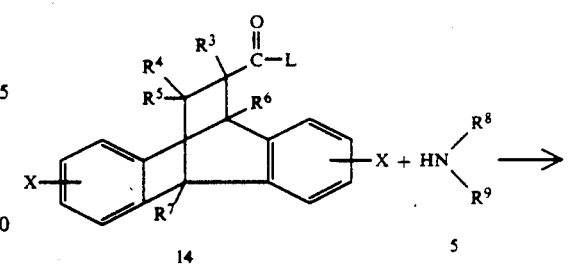
14                        5

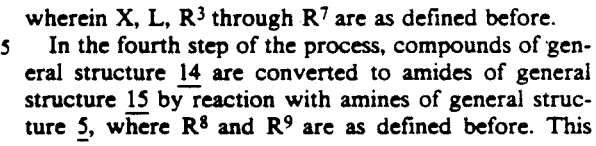
15 wherein X, L, R³ through R⁷ are as defined before.

In the fourth step of the process, compounds of general structure 14 are converted to amides of general structure 15 by reaction with amines of general structure 5, where R⁸ and R⁹ are as defined before. This conversion is best achieved by mixing the reagents neat or in an aprotic solvent such as tetrahydrofuran, methylene chloride, or ether. The temperature of the reaction can vary from 0° C. to reflux of the reaction mixture.

Step 5(i):

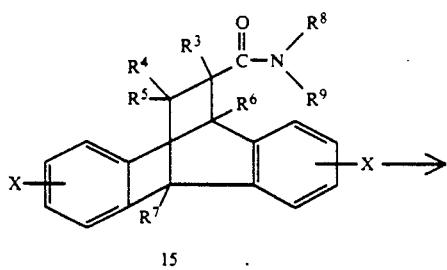

15

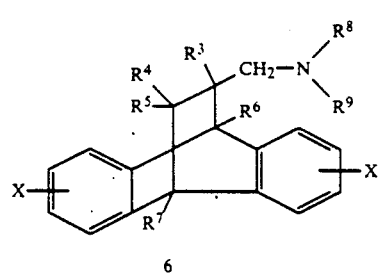

6 wherein X, $R^3$ through $R^9$ are as defined before.

In the fifth step of the process, amides of general structure 150 are converted to amines of general structure 6 by employing reducing agents such as lithium aluminum hydride, sodium borohydride, sodium cyanoborohydride, or other reducing agents familiar to those skilled in the art. This reduction can be accomplished in either protic or aprotic solvents, depending on the reducing agent of choice, and at temperatures ranging from room temperature to reflux of the reaction mixture.

Step 4(ii):

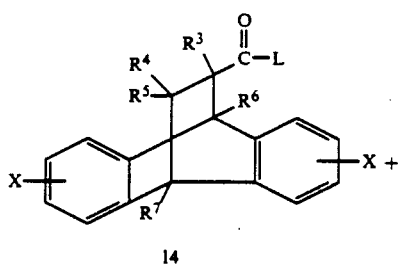

14

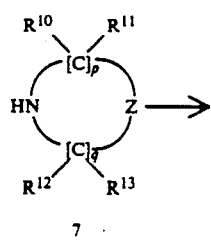

7

-continued

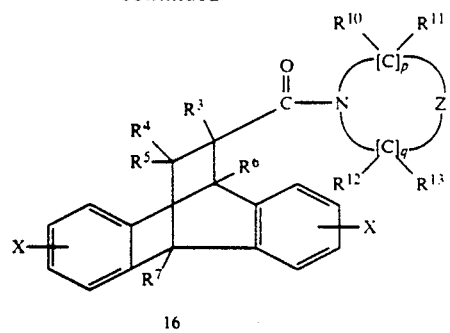

16 wherein p, q, X, Z, L, $R^3$ through $R^7$ and $R^{10}$ through $R^{13}$ are as defined before.

In the fourth step of the process, compounds of general structure 14 are converted to amides of general structure 16 by reaction with amines of general structure 7, where p, q, Z and $R^{10}$ through $R^{13}$ are as defined before. This conversion is best achieved by mixing the reagents neat or in an aprotic solvent such as tetrahydrofuran, methylene chloride, or ether. The temperature of the reaction can vary from 0° C. to reflux of the reaction mixture.

Step 5(ii):

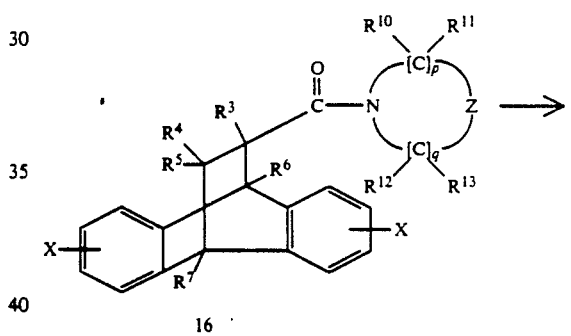

16

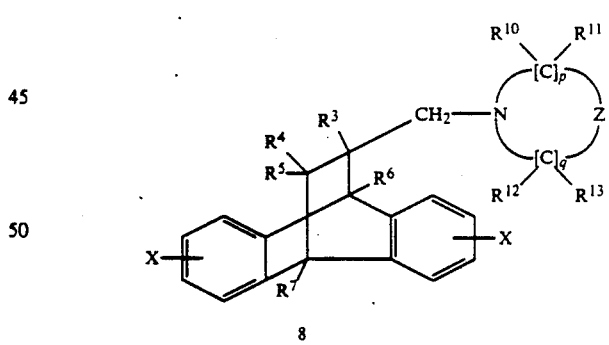

8 wherein p, q, X, L, $R^8$ through $R^7$ and $R^{10}$ through $R^{13}$ are as defined before.

In the fifth step of the process, amides of general structure 16 are converted to amines of general structure 8 by employing reducing agents such as lithium aluminum hydride, sodium borohydride, sodium cyanoborohydride, or other reducing agents familiar to those skilled in the art. This reduction can be accomplished in either protic or aprotic solvents, depending on the reducing agent of choice, and at temperatures ranging from room temperature to reflux of the reaction mixture.

Step 4(iii):

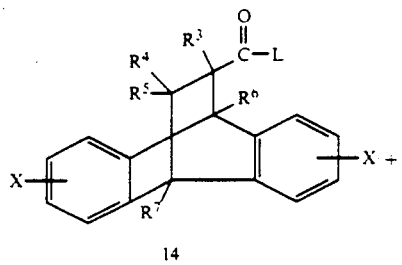

14

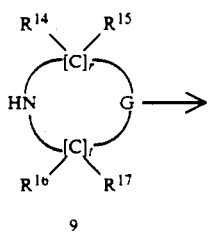

9

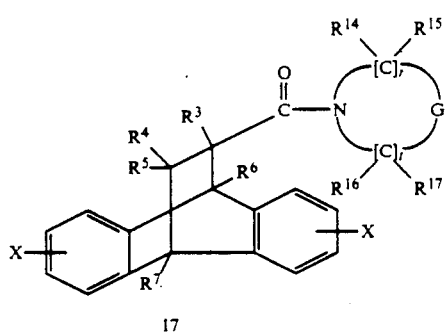

17 wherein r, t, G, X, L, $R^3$ through $R^7$ and $R^{14}$ through $R^{17}$ are as defined before.

In the fourth step of the process compounds of general structure 14 are converted to amides of general structure 17 by reaction with amines of general structure 9, where r, t, G and $R^{14}$ through $R^{17}$; are as defined before. This conversion is best achieved by mixing the reagents neat or in an aprotic solvent such as tetrahydrofuran, methylene chloride, or ether. The temperature of the reaction can vary from 0° C. to reflux of the reaction mixture.

Step 5(iii):

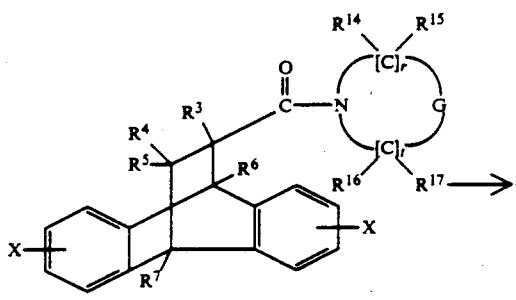

17

—continued

10 wherein r, t, G, X, L, $R^3$ through $R^7$ and $R^{14}$ through $R^{17}$ are as defined before.

In the fifth step of the process, amides of general structure 17 are converted to amines of general structure 10 by employing reducing agents such as lithium aluminum hydride, sodium borohydride, sodium cyanoborohydride, or other reducing agents familiar to those skilled in the art. This reduction can be accomplished in either protic or aprotic solvents, depending on the reducing agent of choice, and at temperatures ranging from room temperature to reflux of the reaction mixture.

EXAMPLE I 9,10-Dihydro-9,10-ethanoanthracene-11-carboxylic Acid

Anthracene (40 gm) was combined with methyl acrylate (30 gm) in a Parr bomb and heated to 150–175° C. for 6 hours. The mixture was allowed to remain in the bomb at room temperature for 72 hours. The mixture was dissolved in methanol (225 ml), treated with a solution of potassium hydroxide (40 gm) in water (40 ml) and heated to reflux for 4 hours. The solution was cooled to room temperature and most of the solvent was removed on a rotary evaporator. The residue was dissolved in water (200 ml), filtered through charcoal and acidified with concentrated hydrochloric acid. The resulting mixture was allowed to stand overnight and the precipitate was filtered. The white solid was dried at 80° and recrystallized from benzene to provide the product (mp=188–189° C.).

EXAMPLE II

N-Diethylaminoethyl-9,10-dihydro-9,10-ethanoanthracene11-carboxamide (Compound No. 10)

9,10-Dihydro-9,10-ethanoanthracene-11-carboxylic acid (25 gm) was combined with thionyl chloride (7.3 ml), benzene (150 ml) and pyridine (7.9 gm) and the resulting mixture was heated to reflux 1.5 hours. The mixture was cooled to room temperature, filtered and treated with 2-diethylaminoethylamine (11.6 gm). The resulting mixture was heated to reflux for 5 hours. The solution was concentrated on a rotary evaporator and the solid residue was suspended in ether, filtered and air dried. The product was recrystallized from ethyl acetate. Analytical data are reported in Table I.

EXAMPLE III 9,10-Dibromo-9,10-Dihydro-9,10-ethanoanthracene-11-methyl-11-carboxylic acid 9,10-Dibromoanthracene (101 gm) was combined with methyl methacrylate (50 ml) and heated in a Parr bomb to 160-180° C. for 8 hours. The resulting material was combined with methanol (500 ml), potassium hydroxide (50 gm) and water (50 ml) and heated to reflux for 4 hours. The mixture was allowed to cool to room temperature and to stand overnight. The solvent was removed on a rotary evaporator and the residue was extracted with water. The aqueous solution was washed with ether and acidified with concentrated hydrochloric acid. The precipitate was filtered and recrystallized from xylenes to provide the product (mp=237-239° C.).

EXAMPLE IV

11-Chloromethyl-9,10-dihydro-9,10-ethanoanthracene

Anthracene (75 gm) was combined with allyl chloride (150 gm) and benzene (375 gm) in a Parr bomb and heated to 220° C. for 13 hours. The contents were filtered and the benzene was removed on a rotary evaporator. The residue was recrystallized from ethanol to provide the product as a white solid (mp=108-111° C.).

EXAMPLE V

N-(2-Hydroxyethyl)-N-methyl-9,10-Dihydro-9,10-ethanoanthracenylmethylamine (Compound No. 12)

11-Chloromethyl-9,10-dihydro-9,10-ethanoanthracene (45 gm) was combined with 2-hydroxyethylmethylamine (45 gm) in xylene (300 ml) and the mixture heated to reflux for 17 days. The mixture was cooled to room temperature and extracted with 1 N hydrochloric acid (3×100 ml). The combined acid solutions were washed with ether (100 ml), made basic with the addition of 50% sodium hydroxide solution and the mixture extracted with ether (3×100 ml). The combined ether solutions were dried over magnesium sulfate and the ether removed on a rotary evaporator. The residue was distilled (220° C. at 7 mm Hg) to yield a colorless oil. The material was dissolved in ether (200 ml) and treated with 6 N hydrochloric acid in isopropyl alcohol (2 ml). The resulting precipitate was filtered and washed with ether to provide the product. Analytical data are reported in Table I.

EXAMPLE VI 9,10-Dihydro-9,10-ethanoanthracene-11-methanol

Anthracene (45.4 gm) was combined with allyl alcohol (90.8 gm) and benzene (260 ml) in a Parr bomb and heated to 210° C. for 12 hours. The benzene was removed on a rotary evaporator and the residue was recrystallized from n-heptane to provide the product as a white solid (mp=104-105° C.).

EXAMPLE VII

11-Bromomethyl-9,10-dihydro-9,10-ethanoanthracene 9,10-Dihydro-9,10-ethanoanthracene-11-methanol (2 gm) was combined with triphenylphosphine dibromide (5.3 gm) in carbon tetrachloride (60 ml). The mixture was heated to reflux 1 hour, filtered, and the filtrate was concentrated on a rotary evaporator. The residue was boiled in n-heptane (75 ml), filtered hot, and the filtrate cooled. The white precipitate was filtered and air dried to provide the product (mp=103-106° C.).

EXAMPLE VIII

11-Bromomethyl-9,10-dihydro-9,10-ethanoanthracene (Alternate Procedure)

9,10-Dihydro-9,10-ethanoanthracene-11-methanol (1.2 gm), imidazole (0.7 gm) and chlorodiphenylphosphine (1.4 gm) were combined in toluene (80 ml) and treated dropwise with bromine (1.0 gm). The mixture was stirred 10 minutes, then extracted with 10% sodium hydroxide (50 ml) and water (50 ml). The toluene was removed on a rotary evaporator and the residue was dissolved in 1:1 methylene chloride/hexane and placed on a silica gel column. The column was eluted with 1:1 methylene chloride/hexane and the eluant removed on a rotary evaporator to give the product.

EXAMPLE IX 4-(9,10-Dihydro-9,10-ethanoanthracenyl)methyl]-1-methylpiperazine (Compound No. 1).

11-Bromomethyl-9,10-dihydro-9,10-ethanoanthracene (0.51 gm), 1-methylpiperazine (1.9 ml) and potassium carbonate (0.20 gm) were combined in hexamethylphosphoramide (5 ml) in a sealed tube and heated to 90° C. for 48 hours. The mixture was extracted between water (25 ml) and ether (50 ml). The ether solution was washed with water (25 ml), then extracted with 3.6 N sulfuric acid (3×25 ml). The combined acid solutions were made basic with the addition of concentrated aqueous ammonia and the resulting mixture was extracted with ether (3×25 ml). The combined ether solutions were dried over magnesium sulfate and the ether removed on a rotary evaporator. The residue was dissolved in anhydrous ether (15 ml) and treated with 3.5% hydrochloric acid in isopropyl alcohol (0.79 ml). The resulting precipitate was filtered, washed with ether (25 ml), and air dried to give the product as a white solid. Analytical data are reported in Table I.

EXAMPLE X

Methyl 9,10-Dihydro-9,10-ethanoanthracene-11-carboxylate

Anthracene (89.0 gm) was combined with methyl acrylate (51.5 gm) and xylenes (500 ml) in a Parr bomb and heated to 210° C. for 12 hours. The solvent was removed on a rotary evaporator and the residue was recrystallized from methanol to provide the product as a white solid (m=113-114° C.).

EXAMPLE XI

4-[9,10-Dihydro-9,10-ethanoanthracenyl)carbonyl]-1-(2-pyrimidyl)piperazine 9,10-Dihydro-9,10-ethanoanthracene-11-carboxylic acid (1.0 gm) was combined with thionyl chloride (10 ml) and heated to reflux 1 hour. The excess thionyl chloride was removed by distillation and the residue was dissolved in anhydrous ether (10 ml). The acid chloride solution was added dropwise to a solution of 1-(2-pyrimidyl)piperazine (2 gm) in ether (90 ml). The resulting mixture was stirred at room temperature for 1 hour. The mixture was washed with 5% sodium bicarbonate solution (2×50 ml) and water (2×50 ml) and the ether solution dried over magnesium sulfate. The ether was removed on a rotary evaporator and the crude material purified using preparative centrifugally accelerated radial thin layer chromatography on silica gel using 5% ethanol in methylene chloride as the eluant to provide the product as a white foam.

EXAMPLE XII

4-[(9,10-ethanoanthracenyl)methyl]-1-(2-pyrimidyl)-piperazine (Compound No. 3)

4-[(9,10-Dihydro-9,10-ethanoanthracenyl)carbonyl-1,2-(2-pyrimidyl)piperazine (0.85 gm) was dissolved in anhydrous tetrahydrofuran and treated with lithium aluminum hydride (0.081 gm). The mixture was heated to reflux for 15 hours. The mixture was cooled in an ice bath and treated with 1 N hydrochloric acid (25 ml). The resulting mixture was washed with ether (2×25 ml) and the combined ether layers extracted with additional 1 N hydrochloric acid (25 ml). The combined acid solutions were made basic by the addition of excess 50% sodium hydroxide solution and extracted with ether (3×35 ml). The combined ether solutions were dried over magnesium sulfate and the ether removed on a rotary evaporator. The residue was dissolved in isopropyl alcohol (10 ml) and treated with 6 N hydrochloric acid in isopropyl alcohol (3 ml). The solution was allowed to stand at room temperature for 1 hour, then it was added dropwise to 200 ml ether. The resulting precipitate was filtered and recrystallized from isopropanol to provide the product as a white solid. Analytical data are reported in Table I.

EXAMPLE XIII

4-[(9,10-Dihydro-9,10-ethanoanthracenyl)methyl]-1-benzylpiperazine (Compound No. 6).

9,10-Dihydro-9,10-ethanoanthracene-11-methanol (1.2 gm) was combined with dimethylformamide (5 ml) and treated with a 60% dispersion of sodium hydride in mineral oil (200 mg). The mixture was stirred at room temperature for 15 minutes.

The resulting solution was then treated with a mixture of 1-benzylpiperazine (1.8 gm) and N-methyl-N-phenylaminotriphenylphosphonium iodide (2.5 gm) in dimethylformamide (10 ml). The reaction mixture was heated to 80° C. for 24 hours. The reaction solution was cooled to room temperature, poured into water (75 ml), and the aqueous mixture was extracted with ether (3×50 ml). The combined ether solutions were extracted with 3.6 N sulfuric acid (3×30 ml) and the combined acid extracts were made basic by the addition of excess concentrated aqueous ammonia. The resulting mixture was extracted with ether (3×50 ml) and the combined ether extracts were dried over magnesium sulfate. After removal of the ether on a rotary evaporator, the crude product was purified by preparative centrifugally accelerated radial thin layer chromatography on silica gel using 5% ethanol in methylene chloride as the eluant to provide a white solid. The solid was dissolved in anhydrous ether (50 ml), treated with 3 N hydrochloric acid in isopropyl alcohol (1 ml), and the resulting precipitate was filtered. The precipitate was recrystallized from ethanol to provide the product as a white solid. Analytical data are reported in Table I.

EXAMPLE XIV

4-Benzyl-1-[(9,10-Dihydro-9,10-ethanoanthracenyl)methyl]piperidine (Compound No. 7).

11-Bromomethyl-9,10-dihydro-9,10-ethanoanthracene (1.2 gm), 4-benzylpiperidine (7.0 gm) and potassium carbonate (0.40 gm) were combined in hexamethylphosphoramide (8 ml) in a sealed tube and heated to 90° C. for 48 hours. The mixture was extracted between water (50 ml) and ether (50 ml). The aqueous layer was extracted with ether (2×50 ml) and the combined ether solutions were washed with water (2×50 ml), then extracted with 3.6 N sulfuric acid (3×50 ml). The combined acid solutions were made basic with the addition of concentrated aqueous ammonia and the resulting mixture was extracted with ether (3×50 ml). The combined ether solutions were dried over magnesium sulfate and the ether and excess 4-benzylpiperidine were removed on a rotary evaporator. The residue was dissolved in methylene chloride (15 ml) and purified by preparative centrifugally accelerated radial thin layer chromatography on silica gel using 90:9:1 methylene chloride/ethanol/triethylamine as the eluant. The crude product was dissolved in isopropyl alcohol (10 ml) and treated with 6 N hydrochloric acid in isopropyl alcohol (0.5 ml). The solution was added dropwise to ether (150 ml) and the resulting solid was filtered. The solid was recrystallized from isopropyl alcohol to provide the product as a white solid. Analytical data are reported in Table I.

EXAMPLE XV

1-[(9,10-Dihydro-9,10-ethanoanthracenyl)methyl]-piperidine (Compound No. 9)

11-Chloromethyl-9,10-dihydro-9,10-ethanoanthracene (26 gm) was combined with piperidine (26 gm) in xylene (200 ml) and the mixture heated to reflux for two weeks. The mixture was cooled to room temperature and extracted with 1 N hydrochloric acid (3×75 ml). The combined acid solutions were made basic with the addition of 50% sodium hydroxide solution and the mixture extracted with ether (3×100 ml). The combined ether solutions were dried over magnesium sulfate and the ether removed on a rotary evaporator. The residue was distilled (220° C. at 7 mm Hg) to yield a white solid (mp=120° C.). The material was dissolved in ether (400 ml) and treated with 6 N hydrochloric acid in isopropyl alcohol (2 ml). The resulting precipitate was filtered to provide the product. Analytical data are reported in Table I.

TABLE I

| Compound Number | Name | Structure | Method of Preparation | Elemental Analysis | | Melting Point |
| --- | --- | --- | --- | --- | --- | --- |
| | | | | Theor. | Found | |
| 1 | 4-[(9,10-dihydro-9,10-ethanoanthracenyl)methyl]-1-methylpiperazine. 1.5HCl.0.8H$_2$O | 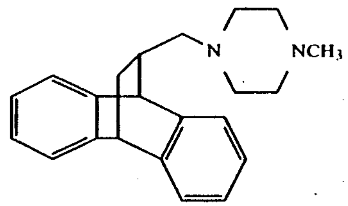 | VI, VII, IX or X, I, XI, XII | C 68.24<br>H 7.57<br>N 7.23 | 68.25<br>7.53<br>7.11 | 236-241° C. |
| 2 | 4-[(9,10-dihydro-9,10-ethanoanthracenyl)methyl]-1-(2-hydroxyethyl)-piperazine.1.9HCl.0.6H$_2$O | 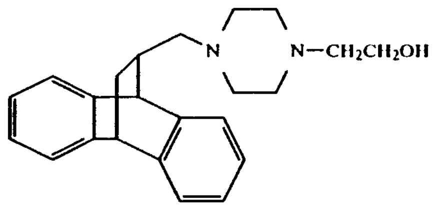 | VI, VII, IX | C 64.13<br>H 7.30<br>N 6.50 | 64.13<br>7.29<br>6.50 | 282-286° C. |
| 3 | 4-[(9,10-dihydro-9,10-ethanoanthracenyl)methyl]-1-(2-pyrimidyl)piperazine.2HCl.0.9H$_2$O | 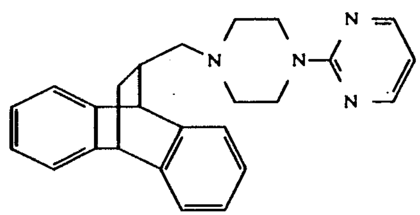 | X, XII | C 63.58<br>H 6.36<br>N 11.80 | 63.66<br>6.36<br>11.27 | 276-279° C. |
| 4 | 4-[(9,10-dihydro-9,10-ethanoanthracenyl)methyl]-1,4-diazabicyclo[4.3.0]-nonane.1.9HCl.1.4H$_2$O | 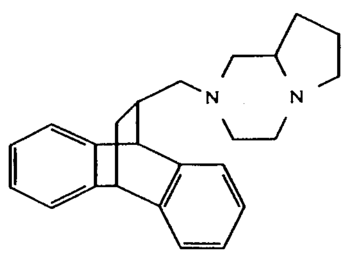 | X, XII | C 65.58<br>H 7.51<br>N 6.37 | 65.59<br>7.35<br>6.21 | 213-216° C. |

TABLE I-continued

| Compound Number | Name | Structure | Method of Preparation | Elemental Analysis | | Melting Point |
|---|---|---|---|---|---|---|
| | | | | Theor. | Found | |
| 5 | 4-[(9,10-dihydro-9,10-ethanoanthracenyl)carbonyl]-1-methylpiperazine. 0.3EtOH | 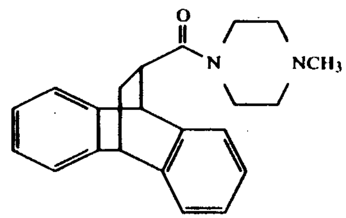 | X, XI | C 78.25<br>H 7.54<br>N 8.05 | 78.36<br>7.38<br>7.58 | 73-76° C. |
| 6 | 4-[(9,10-dihydro-9,10-ethanoanthracenyl)methyl]-1-benzylpiperazine. 2HCl.0.9H₂O | 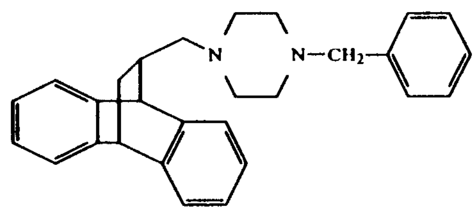 | XIII | C 71.27<br>H 6.94<br>N 5.94 | 71.25<br>6.98<br>5.89 | 254-256° C. |
| 7 | 4-benzyl-1-[(9,10-dihydro-9,10-ethanoanthracenyl)methyl]piperidine | 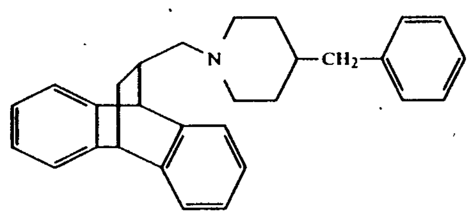 | VI, VII, XIV | C 88.50<br>H 7.94<br>N 3.56 | 88.30<br>8.14<br>3.50 | 136-137° C. |
| 8 | 1-[(9,10-dihydro-9,10-ethanoanthracenyl)methyl]-4-phenylpiperidine | 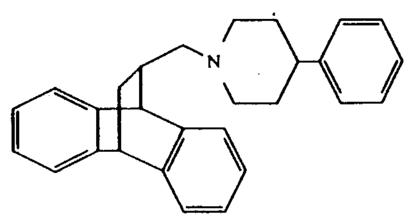 | VI, VII, XIV | C 88.61<br>H 7.70<br>N 3.69 | 88.23<br>7.96<br>3.52 | 108-110° C. |

TABLE I-continued

| Compound Number | Name | Structure | Method of Preparation | Elemental Analysis Theor. | Elemental Analysis Found | Melting Point |
|---|---|---|---|---|---|---|
| 9 | 1-[(9,10-dihydro-9,10-ethanoanthracenyl)methyl]piperidine.HCl.0.3H$_2$O | (piperidine-substituted ethanoanthracene structure) | IV, XV | C 76.92<br>H 7.79<br>N 4.08 | C 76.92<br>H 7.79<br>N 3.99 | 245–250° C. |
| 10 | N-diethylaminoethyl-9,10-dihydro-9,10-ethanoanthracene-11-carboxamide.HCl | O=C−NH−CH$_2$CH$_2$−N(CH$_2$CH$_3$)$_2$ (ethanoanthracene) | I, II | C 51.76<br>H 5.33<br>N 6.30 | C 51.77<br>H 5.25<br>N 6.37 | 136–137.5° C. |
| 11 | N-diethylaminoethyl-9,10-dibromo-9,10-dihydro-9,10-ethanoanthracene-11-methyl-11-carboxamide.HCl | O=C−NH−CH$_2$CH$_2$−N(CH$_2$CH$_3$)$_2$ with CH$_3$, Br, Br substituents | III, II | C 51.77<br>H 5.25<br>Cl 6.37 | C 51.76<br>H 5.33<br>Cl 6.30 | 170–172° C. |
| 12 | N-(2-hydroxyethyl)-N-methyl-9,10-dihydro-9,10-ethanoanthracenyl-methylamine.HCl.H$_2$O | CH$_3$−N−CH$_2$CH$_2$OH (ethanoanthracene) | IV, V | C 72.82<br>H 7.33<br>N 4.25 | C 72.72<br>H 7.16<br>N 4.12 | 203–204° C. |

Assay for Effect on cGMP

Male Swiss-Webster mice (17-24 g) were injected intracisternally (i.c.t.) with glycine agonists 10 minutes prior to sacrifice by focussed microwave irradiation. Compounds of the invention were co-injected intracisternally with the agonist. For intracisternal injections, all agonists were dissolved in HCl and diluted with isotonic saline prior to adjustment of the pH to between 6 and 7 with NaOH. The compounds of the invention were dissolved in isotonic saline and all compounds were administered in a volume of 5 μl. The agonist doses were obtained by making serial dilutions of a concentrated solution of drug until intracisternal injections of 5 μl resulted in no more than 10% mortality during the first 15 minutes after injection.

Hydrochloric acid in extracts of the cerebellum were freeze-dried for assay of cGMP with a commercial RIA kit (NEN). Protein determinations (Lowery) and statistics (Dunett's t-test) were performed as described previously [P. L. Wood et al., Neurochem., 19, 975-982 (1980)]. Groups consisted of 7-10 mice. Results are reported in Table II.

TABLE II

| Compound | Cerebellar cGMP (pmol/mg protein + SEM) |
|---|---|
| Saline | 3.09 ± 0.48 |
| D-Serine (200 μg) | 17.2 ± 3.52 |
| Compound No. 1 (25 μg) | 3.8 ± 1.0 |
| D-Serine (200 μg) + Compound No. 1 (25 μg) | 5.1 ± 0.93 |

Forebrain Ischemia Assay

Male Mongolian gerbils, 50-70 gm, were used as subjects. Compound No. 1 (30 mg/kg) was injected i.p. 30 minutes prior to carotid occlusion into 6 gerbils. In preparation for surgical procedures, the animals were lightly anesthetized with halothane and placed upside down on a heated pad with their snout within a nosecone. Nitrous oxide (70%): oxygen (30%) plus 0.5% halothane was circulated through the nosecone to provide continuous anesthesia throughout the surgical procedure. A midline incision was made in the neck and the carotid arteries were exposed. A length of suture thread was placed under each carotid. The thread was then tightened around each carotid and pressure applied to the thread to insure flow was occluded. Flow was occluded for 5 minutes and then the thread was removed. The carotids were visually inspected to confirm that reflow had occurred. The wound was then closed with autoclips and the gerbils allowed to recover. Following surgery, the gerbils were kept alive for 7 days. They were anesthetized with 100 mg/kg sodium pentobarbital and perfused transcardially with saline (with heparin) followed by buffered formalin. The brain was removed, trimmed and prepared for histological processing. Sections (10 microns) were stained with thionin. At 7 days following the ischemic insult, damaged neurons have been cleared away by glia and the extent of damage can be ascertained within the vulnerable CA1 region of the hippocampus. The degree of lesion in the CA1 region of the hippocampus was quantified by counting the pyramidal cell bodies in a 0.5 mm length of CA1 on the section corresponding to P 1.7 mm in the atlas of Loskota, Lomax and Verity [W. J. Loskota et al, *A Stereotaxic Atlas of the Monolian Gerbil Brain*, Ann Arbor Science Publishers, Ann Arbor, p. 77, (1974)].

The cell loss was significantly reduced in the gerbils given Compound No. 1 ($p<0.01$).

Also embraced within this invention is a class of pharmaceutical compositions comprising one or more compounds of Formula I in association with one or more non-toxic, pharmaceutically acceptable carriers and/or diluents and/or adjuvants (collectively referred to herein as "carrier" materials) and, if desired, other active ingredients. The compounds of the present invention may be administered by any suitable route, preferably in the form of a pharmaceutical composition adapted to such a route, and in a dose effective for the treatment intended. Therapeutically effective doses of the compounds of the present invention required to prevent or arrest the progress of the medical condition are readily ascertained by one of ordinary skill in the art. The compounds and composition may, for example, be administered intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a therapeutically-effective amount of the active ingredient. Examples of such dosage units are tablets or capsules. A suitable daily dose for a mammal may vary widely depending on the condition of the patient, body weight and other factors.

The active ingredient may also be administered by injection as a composition wherein, for example, saline, dextrose or water may be used as a suitable carrier. A suitable daily dose is from about 0.1 to 100 mg/kg body weight injected per day in multiple doses depending on the disease being treated. A preferred daily dose would be from about 1 to 30 mg/kg body weight. Compounds indicated for prophylactic therapy will preferably be administered in a daily dose generally in a range from about 0.1 mg to about 100 mg per kilogram of body weight per day. A more preferred dosage will be a range from about 1 mg to about 100 mg per kilogram of body weight. Most preferred is a dosage in a range from about 1 to about 50 mg per kilogram of body weight per day. A suitable dose can be administered, in multiple sub-doses per day. These sub-doses may be administered in unit dosage forms. Typically, a dose or sub-dose may contain from about 1 mg to about 100 mg of active compound per unit dosage form. A more preferred dosage will contain from about 2 mg to about 50 mg of active compound per unit dosage form. Most preferred is a dosage form containing from about 3 mg to about 25 mg of active compound per unit dose.

The dosage regimen for treating a disease condition with the compounds and/or compositions of this invention is selected in accordance with a variety of factors, including the type, age, weight, sex and medical condition of the patient, the severity of the disease, the route of administration, and the particular compound employed, and thus may vary widely.

For therapeutic purposes, the compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. A method for treating a patient afflicted by or susceptible to a neurodegenerative disorder or neurotoxic injury, said method comprising administering to the patient a therapeutically-effective amount of a compound of Formula I:

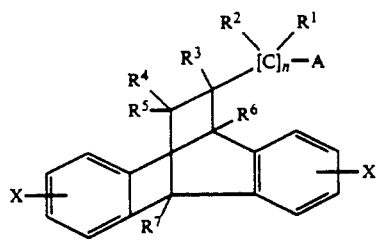

wherein A is

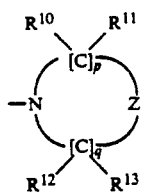

wherein each of $R^1$ and $R^2$ is independently selected from hydrido, alkyl, cycloalkyl, cycloalkylalkyl, aralkyl, aryl, hydroxyalkyl, alkoxyalkyl and halo; wherein $R^1$ and $R^2$ may be taken together to form oxo; wherein each of $R^3$ through $R^7$ is independently selected from hydrido, alkyl, hydroxy, cycloalkyl, cycloalkylalkyl, aralkyl, aryl, alkoxy, alkoxyalkyl, aryloxy, aralkoxy, hydroxyalkyl, halo and haloalkyl; wherein $R^4$ and $R^5$ may be taken together to form oxo; wherein n is a number selected from zero to five, inclusive; wherein each X is independently one or more groups selected from hydrido, hydroxy, alkyl, cycloalkyl, cycloalkylalkyl, aralkyl, aryl, alkoxy, aralkoxy, aryloxy, alkoxyalkyl, haloalkyl, hydroxyalkyl, halo, cyano, amino, monoalkylamino, dialkylamino, nitro, carboxy, carboxyalkyl and alkanoyl; wherein each of $R^{10}$ through $R^{13}$ is independently selected from hydrido, alkyl, cycloalkyl, cycloalkylalkyl, aralkyl, aryl, alkoxyalkyl, hydroxyalkyl and halo; wherein $R^{10}$ and $R^{11}$ may be taken together to form oxo; wherein $R^{12}$ and $R^{13}$ may be taken together to form oxo; wherein each of p and q is a number selected from one to four, inclusive; wherein Z is selected from O, S, and $>N-R^{18}$; wherein $R^{18}$ may be selected from hydrido, alkyl, cycloalkyl, cycloalkylalkyl, aryl, aralkyl, heteroaryl, alkoxyalkyl, hydroxyalkyl, alkanoyl, aralkanoyl, aroyl, aminoalkyl, monoalkylaminoalkyl and dialkylaminoalkyl; wherein $R^{18}$ together with one of $R^{10}$ through $R^{13}$ may form a fused heterocyclic ring containing five to about eight ring members; or a pharmaceutically-acceptable salt thereof.

2. The method of claim 1 wherein each of $R^1$ and $R^2$ is independently selected from hydrido, alkyl, cycloalkyl, cycloalkylalkyl, aralkyl, aryl, hydroxyalkyl, alkoxyalkyl and halo; wherein $R^1$ and $R^2$ may be taken together to form oxo; wherein each of $R^3$ and $R^7$ is independently selected from hydrido, alkyl, hydroxy, cycloalkyl, cycloalkylalkyl, aralkyl, aryl, alkoxy, alkoxyalkyl, aryloxy, aralkoxy, hydroxyalkyl, halo and haloalkyl; wherein $R^4$ and $R^5$ may be taken together to form oxo; wherein n is a number selected from zero to five, inclusive; wherein each X is independently one or more groups selected from hydrido, hydroxy, alkyl, cycloalkyl, cycloalkylalkyl, aralkyl, aryl, alkoxy, aralkoxy, aryloxy, alkoxyalkyl, haloalkyl, hydroxyalkyl, halo, cyano, amino, monoalkylamino, dialkylamino, nitro, carboxy, carboxyalkyl and alkanoyl; or a pharmaceutically-acceptable salt thereof.

3. The method of claim 2 wherein each of $R^1$ and $R^2$ is independently selected from hydrido, alkyl, cycloalkyl, cycloalkylalkyl, aralkyl, aryl, hydroxyalkyl, alkoxyalkyl and halo; wherein $R^1$ and $R^2$ may be taken together to form oxo; wherein each of $R^3$ through $R^7$ is independently selected from hydrido, alkyl, hydroxy, cycloalkyl, cycloalkylalkyl, phenalkyl, phenyl, alkoxy, alkoxyalkyl, phenoxy, phenalkoxy, hydroxyalkyl, halo and haloalkyl; wherein $R^4$ and $R^5$ may be taken together to form oxo; wherein n is a number from zero to five, inclusive; wherein each X is independently one or more groups selected from hydrido, hydroxy, alkyl, cycloalkyl, cycloalkylalkyl, phenalkyl, phenyl, alkoxy, phenalkoxy, phenoxy, alkoxyalkyl, haloalkyl, hydroxyalkyl, halo, cyano, amino, monoalkylamino, dialkylamino, carboxy, carboxyalkyl and alkanoyl; or a pharmaceutically-acceptable salt thereof.

4. The method of claim 3 wherein each of $R^1$ and $R^2$ is independently selected from hydrido, loweralkyl, phenylloweralkyl, phenyl and loweralkoxy-loweralkyl; wherein $R^1$ and $R^2$ may be taken together to form oxo; wherein each of $R^3$ through $R^7$ is independently selected from hydrido, loweralkyl, hydroxy, cycloalkyl of three to eight carbon atoms, cycloalkylalkyl of four to eight carbon atoms, phenylloweralkyl, phenyl, loweralkoxy, loweralkoxyloweralkyl, phenoxy, phenalkoxy, hydroxyloweralkyl, halo and haloloweralkyl; wherein $R^4$ and $R^5$ may be taken together to form oxo; wherein n is a number selected from zero to five, inclusive; wherein each X is independently one or more groups selected from hydrido, hydroxy, loweralkyl, cycloalkyl of three to about eight carbon atoms, cycloalkylalkyl of four to about eight carbon atoms, phenylloweralkyl, phenyl, loweralkoxy, phenoxy, loweralkoxyloweralkyl, haloloweralkyl, hydroxyloweralkyl, halo, carboxy, carboxyloweralkyl and loweralkanoyl; or a pharmaceutically-acceptable salt thereof.

5. The method of claim 4 wherein each of $R^1$ and $R^2$ is independently selected from hydrido, loweralkyl, benzyl and phenyl; wherein $R^1$ and $R^2$ may be taken together to form oxo; wherein n is selected from zero to two, inclusive; wherein each of $R^3$ and $R^7$ is independently selected from hydrido, loweralkyl, hydroxy, benzyl, phenyl, loweralkoxy, phenoxy, benzyloxy, halo and haloloweralkyl; wherein each X is independently one or more groups selected from hydrido, hydroxy, loweralkyl, benzyl, phenyl, loweralkoxy, phenoxy, haloloweralkyl, halo and loweralkanoyl; or a pharmaceutically-acceptable salt thereof.

6. The method of claim 5 wherein each of $R^1$ and $R^2$ is independently hydrido or methyl; wherein $R^1$ and $R^2$ may be taken together to form oxo; wherein each of $R^3$ through $R^7$ is independently selected from hydrido, methyl, ethyl, hydroxy, methoxy, halo and trihalomethyl; wherein n is one or two; and wherein each X is independently one or more groups selected from hydrido, methyl, ethyl, hydroxy, methoxy, trihalomethyl and halo; or a pharmaceutically-acceptable salt thereof.

7. The method of claim 1 wherein said compound is selected from a family of compounds of Formula III:

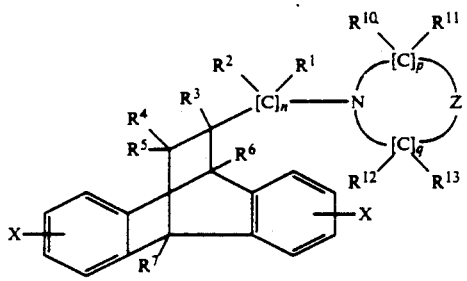

wherein each of $R^1$, $R^2$ and $R^{10}$ through $R^{13}$ is independently selected from hydrido, alkyl, cycloalkyl, cycloalkylalkyl, aralkyl, aryl, alkoxyalkyl, hydroxyalkyl and halo; wherein $R^{10}$ and $R^{11}$ may be taken together to form oxo; wherein $R^{12}$ and $R^{13}$ may be taken together to form oxo; wherein $R^1$ and $R^2$ may be taken together to form oxo; wherein each of $R^3$ and $R^7$ is independently selected from hydrido, alkyl, hydroxy, cycloalkyl, cycloalkyl alkyl, aralkyl, aryl, alkoxy, alkoxyalkyl, aryloxy, aralkoxy, hydroxyalkyl, halo and haloalkyl; wherein $R^4$ and $R^5$ may be taken together to form oxo; wherein n is a number selected from zero to five, inclusive; wherein each of p and q is a number selected from one to four, inclusive; wherein Z is selected from O, S, and $>N-R^{18}$; wherein $R^{18}$ may be selected from hydrido, alkyl, cycloalkyl, cycloalkylalkyl, aryl, aralkyl, heteroaryl, alkoxyalkyl, hydroxyalkyl, alkanoyl, aralkanoyl, aroyl, aminoalkyl, monoalkylaminoalkyl an dialkylaminoalkyl; wherein $R^{18}$ together with one of $R^{10}$ through $R^{13}$ may form a fused heterocyclic ring containing five to about eight ring members; wherein each X is independently one or more groups selected from hydrido, hydroxy, alkyl, cycloalkyl, cycloalkylalkyl, aralkyl, aryl, alkoxy, aralkoxy, aryloxy, alkoxyalkyl, haloalkyl, hydroxyalkyl, halo, cyano, amino, monoalkylamino, dialkylamino, nitro, carboxy, carboxyalkyl and alkanoyl; or a pharmaceutically-acceptable salt thereof.

8. The method of claim 7 wherein each of $R^1$, $R^2$ and $R^{10}$ through $R^{13}$ is independently selected from hydrido, alkyl, cycloalkyl, cycloalkylalkyl, phenalkyl, phenyl, alkoxyalkyl, hydroxyalkyl and halo; wherein $R^1$ and $R^2$ may be taken together to form oxo; wherein each of $R^3$ through $R^7$ is independently selected from hydrido, alkyl, hydroxy, cycloalkyl, cycloalkylalkyl, phenalkyl, phenyl, alkoxy, alkoxyalkyl, phenoxy, phenalkoxy, hydroxyalkyl, halo and haloalkyl; wherein $R^4$ and $R^5$ may be taken together to form oxo; wherein n is a number from zero to five, inclusive; wherein each of p and q is a number selected from one to four, inclusive; wherein Z is selected from O, S and $>N-R^{18}$; wherein $R^{18}$ may be selected from hydrido, alkyl, cycloalkyl, cycloalkylalkyl, phenyl, phenalkyl, heteroaryl, alkoxyalkyl, hydroxyalkyl, alkanoyl, phenalkanoyl, aroyl, aminoalkyl, monoalkylaminoalkyl and dialkylaminoalkyl; wherein $R^{18}$ together with one of $R^{10}$ through $R^{13}$ form a fused heterocyclic ring containing five to about eight ring members; wherein each X is independently one or more groups selected from hydrido, hydroxy, alkyl, cycloalkyl, cycloalkylalkyl, phenalkyl, phenyl, alkoxy, phenalkoxy, phenoxy, alkoxyalkyl, haloalkyl, hydroxyalkyl, halo, cyano, amino, monoalkylamino, dialkylamino, carboxy, carboxyalkyl and alkanoyl; or a pharmaceutically-acceptable salt thereof.

9. The method of claim 8 wherein each of $R^{10}$ through $R^{13}$ is independently selected from hydrido, loweralkyl, cycloalkyl of three to about eight carbon atoms, cycloalkylalkyl of four to about eight carbon atoms, phenylloweralkyl, phenyl, loweralkoxyloweralkyl, hydroxyloweralkyl and halo; wherein each of $R^1$ and $R^2$ is independently selected from hydrido, loweralkyl, phenylloweralkyl, phenyl and loweralkoxyloweralkyl; wherein $R^1$ and $R^2$ may be taken together to form oxo; wherein each of $R^3$ through $R^7$ is independently selected from hydrido, loweralkyl, hydroxy, cycloalkyl of three to eight carbon atoms, cycloalkylalkyl of four to eight carbon atoms, phenylloweralkyl, phenyl, loweralkoxy, loweralkoxyloweralkyl, phenoxy, phenalkoxy, hydroxyloweralkyl, halo and haloloweralkyl; wherein $R^4$ and $R^5$ may be taken together to form oxo; wherein n is a number selected from zero to five, inclusive; wherein each of p and q is two or three; wherein Z is selected from O, S, $>N-R^{18}$; wherein $R^{18}$ may be selected from hydrido, loweralkyl, cycloalkyl of three to about eight carbon atoms, cycloalkylalkyl of four to about eight carbon atoms, phenyl, phenylloweralkyl, loweralkoxyloweralkyl, hydroxyloweralkyl, loweralkanoyl and heteroaryl selected from saturated, partially unsaturated and fully unsaturated heterocyclic rings containing five to seven ring members of which one or two ring members are selected from oxygen atom and nitrogen atom; wherein $R^{18}$ together with one of $R^{10}$ through $R^{13}$ may form a fused heterocyclic ring containing five or six ring members; wherein each X is independently one or more groups selected from hydrido, hydroxy, loweralkyl, cycloalkyl of three to about eight carbon atoms, cycloalkylalkyl of four to about eight carbon atoms, phenylloweralkyl, phenyl, loweralkoxy, phenoxy, loweralkoxyloweralkyl, haloloweralkyl, hydroxyloweralkyl, halo, carboxy, carboxyloweralkyl and loweralkanoyl; or a pharmaceutically-acceptable salt thereof.

10. The method of claim 9 wherein said compound is selected from a family of compounds of Formula IV:

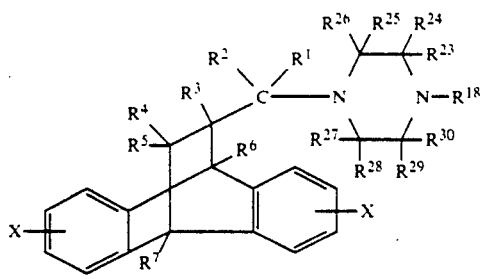

(IV)

wherein each of $R^1$ and $R^2$ is independently selected from hydrido, loweralkyl, benzyl and phenyl; wherein $R^1$ and $R^2$ may be taken together to form oxo; wherein each of $R^3$ through $R^7$ is independently selected from hydrido, loweralkyl, hydroxy, benzyl, phenyl, benzyl, loweralkoxy, phenoxy, benzyloxy, halo and halolower-alkyl; wherein $R^{18}$ may be selected from hydrido, loweralkyl, cycloalkyl of five or six carbon atoms, cycloalkylalkyl of six or seven carbon atoms, phenyl, hydroxyloweralkyl, and heteroaryl selected from saturated or fully unsaturated heterocyclic rings containing five to seven ring members of which one or two ring members are nitrogen atom; wherein each X is independently one or more groups selected from hydrido, hydroxy, loweralkyl, benzyl, phenyl, loweralkoxy, phenoxy, haloloweralkyl, halo, and loweralkanoyl; and wherein each of $R^{23}$ through $R^{30}$ is independently selected from hydrido, loweralkyl, benzyl, phenyl and halo; wherein $R^{18}$ together with one of $R^{23}$, $R^{24}$, $R^{29}$ or $R^{30}$ may form a fused heterocyclic ring containing five or six ring members; or a pharmaceutically-acceptable salt thereof.

11. The method of claim 10 wherein each of $R^1$ and $R^2$ is independently hydrido or methyl; wherein $R^1$ and $R^2$ may be taken together to form oxo; wherein each of $R^3$ through $R^7$ is independently selected from hydrido, methyl, ethyl, hydroxy, methoxy, halo and trihalomethyl; wherein $R^{18}$ is selected from hydrido, methyl, ethyl, hydroxyethyl, benzyl, pyridyl and pyrimidyl; wherein each of $R^{23}$ through $R^{30}$ is independently selected from hydrido, methyl, ethyl and trihalomethyl; wherein $R^{18}$ together with one of $R^{23}$, $R^{24}$, $R^{29}$ or $R^{30}$ may form a fused heterocyclic ring containing five or six ring members; and wherein each X is independently one or more groups selected from hydrido, methyl, ethyl, hydroxy, methoxy, trihalomethyl and halo; or a pharmaceuticallyacceptable salt thereof.

12. The method of claim 11 wherein said compound is selected from 4-[(9,10-dihydro-9,10-ethanoanthracenyl)methyl]1-methylpiperazine; 4-[(9,10-dihydro-9,10-ethanoanthracenyl)methyl]-1-(2-hydroxyethyl)-piperazine; 4-[(9,10-dihydro-9,10-ethanoanthracenyl)-methyl]-1-(2-pyrimidyl)piperazine; 4-[(9,10-dihydro-9,10-ethanoanthracenyl)methyl]-1,4-diazabicyclo[4.3.0]-nonane; 4-[(9,10-dihydro-9,10-ethanoanthracenyl)carbonyl]-1-methylpiperazine; and 4-[(9,10-dihydro-9,10-ethanoanthracenyl)methyl]-1-benzylpiperazine.

13. The method of claim 12 wherein said compound is selected from 4-[(9,10-dihydro-9,10-ethanoanthracenyl)methyl]-1-(2-pyrimidyl)piperazine; 4-[(9,10-dihydro-9,10-ethanoanthracenyl)methyl]-1,4-diazabicyclo[4.3.0]-nonane; and 4-[(9,10-dihydro-9,10-ethanoanthracenyl)methyl]-1-benzylpiperazine.

14. The method of claim 1 wherein said patient is treated for a neurodegenerative disorder.

15. The method of claim 1 wherein said patient is treated for neurotoxic injury.

* * * * *